(12) United States Patent
Winge et al.

(10) Patent No.: US 10,889,630 B2
(45) Date of Patent: Jan. 12, 2021

(54) METHOD OF SEPARATING FACTOR VIII FROM BLOOD PRODUCTS

(71) Applicant: OCTAPHARMA AG, Lachen (CH)

(72) Inventors: Stefan Winge, Arsta (SE); Per Rosen, Molndal (SE); Alex Scheepers, Sollentuna (SE)

(73) Assignee: OCTAPHARMA AG, Lachen (CH)

( * ) Notice: Subject to any disclaimer, the term of this patent is extended or adjusted under 35 U.S.C. 154(b) by 78 days.

(21) Appl. No.: 16/077,195

(22) PCT Filed: Feb. 10, 2017

(86) PCT No.: PCT/EP2017/053045
§ 371 (c)(1),
(2) Date: Aug. 10, 2018

(87) PCT Pub. No.: WO2017/137583
PCT Pub. Date: Aug. 17, 2017

(65) Prior Publication Data
US 2020/0010532 A1    Jan. 9, 2020

(30) Foreign Application Priority Data

Feb. 11, 2016  (EP) ..................................... 16155199

(51) Int. Cl.
| | |
|---|---|
| *A61K 38/00* | (2006.01) |
| *C07K 14/755* | (2006.01) |
| *B01D 15/38* | (2006.01) |
| *C07K 1/22* | (2006.01) |
| *C07K 16/36* | (2006.01) |

(52) U.S. Cl.
CPC ........ *C07K 14/755* (2013.01); *B01D 15/3809* (2013.01); *C07K 1/22* (2013.01); *C07K 16/36* (2013.01); *C07K 2317/55* (2013.01)

(58) Field of Classification Search
None
See application file for complete search history.

(56) References Cited

FOREIGN PATENT DOCUMENTS

| | | |
|---|---|---|
| RU | 2567811 C2 | 11/2015 |
| WO | 2009/156430 A1 | 12/2009 |
| WO | 2014/083510 A1 | 6/2014 |
| WO | 2014/147386 A1 | 9/2014 |
| WO | 2015/107222 A1 | 7/2015 |
| WO | WO-2015107222 A1 * | 7/2015 ........... C07K 14/755 |

OTHER PUBLICATIONS

Hellstern et al. Transfus Med Hemother 2011;38:65-70; 2010.*
Elmar et al. Coagulation & Fibrinolysis Jul. 2015—vol. 26—Issue 5—p. 515-521.*
PCT, International Search Report, International Application No. PCT/EP2017/053045, 4 pages (dated Apr. 20, 2017).
PCT, Written Opinion of the International Searching Authority, International Application Application No. PCT/EP2017/053045, 5 pages (dated Apr. 20, 2017).
Burnouf-Radosevich, M. et al., "Chromatographic Preparation of a Therapeutic Highly Purified von Willebrand Factor Concentrate from Human Cryoprecipitate," 11 pages (1992).
Fay, P.J., "Factor VII Structure and Function," International Journal of Hematology, vol. 83, pp. 103-108 (2006).
Knör, S. et al., "Efficient factor VIII affinity purification using a small synthetic ligand," Journal of Thrombosis and Haemostasis, vol. 6, pp. 470-477 (2008).
Pflegerl, K. et al., "Mutational analysis of a blood coagulation factor VIII-binding peptide," Journal of Peptide Research, vol. 59, pp. 174-182 (2002).
Chiu et al., Mapping the Interaction between Factor VIII and von Willebrand Factor by Electron Microscopy and Mass Spectrometry, Blood, 2015; vol. 126(8), pp. 935-938.
ECAT Assay Procedures a Manual of Laboratory Techniques, Springer Science + Business Media, B.V., 228 pages, Oct. 2012.
Eriksson et al., The manufacturing process for B-domain deleted recombinant Factor VIII, Seminars in Hematology, 2001, vol. 38, No. 2, Suppl. 4 pp. 24-31.
Farrugia et al., Biotechnology and plasma fractionation industry. The impact of advances in the production of coagulation Factor VIII. Biotechnology, 1993, vol. 3, No. 1.
Fay, Factor VIII Function and structure, International Journal of Hematology vol. 83 2006, pp. 103-108.
Fischer et al., Structural analysis of recombinant von Willebrand factor: identification of hetero- and homo-dimers, FEBS Letters 1994, vol. 351, pp. 345-348.
Furlan, Von Willebrand factor: molecular size and functional activity, Ann. Hematol. 1996 vol. 72(6), pp. 341-348.
Girma et al., Assay of Factor VIII antigen (VIII:CAg) in 294 Haemophilia A patients by a new commercial ELISA using monoclonal antibodies, Haemophilia, 1998, vol. 4, pp. 98-103.
McCue et al., Application of a novel affinity adsorbent for the capture and purification of recombinant Factor VIII compounds, Journal of Chromatography A, vol. 1216, 2009, pp. 7824-7830.
Muyldermans, Single domain camel antibodies: current status, Reviews in Moleculer Biotechnology, vol. 74, 2001, pp. 277-302.
Palareti et al., Fibrinogen assays: a collaborative study of six different methods, Clinical Chemistry, 1991; vol. 37 pp. 714-719.
Rosen, Assay of Factor VIII:C with a chromogenic substrate, Scand J Haemetol-Suppl 40, vol. 33, 1984, pp. 139-145.

(Continued)

*Primary Examiner* — Jeanette M Lieb
(74) *Attorney, Agent, or Firm* — Thompson Hine LLP

(57) ABSTRACT

The invention provides a method for separating a Factor VIII (FVIII) protein from a first composition comprising the FVIII protein, which contains at least the light chain of FVIII, and a von-Willebrand-Factor (vWF) protein which comprises at least the FVIII binding domain of vWF, wherein the FVIII protein can form a complex with the vWF protein, the method comprising the steps: contacting the first composition with an affinity resin comprising a ligand and a matrix, wherein the ligand has an affinity to the light chain of FVIII, and separating the affinity resin from the mixture to obtain a modified first composition and a second composition, wherein the second composition contains the affinity resin, and a complex of the FVIII protein and the vWF protein.

17 Claims, 7 Drawing Sheets

(56) References Cited

OTHER PUBLICATIONS

Rossi et al., Method for the determination of functional (clottable) fibrinogen by the new family of ACL coagulometers. Thrombosis Research, 1988, vol. 52, pp. 453-468.

Svensson et al., Evaluation of the metal binding site in a recombinant coagulation factor VIII identifies two sites with unique metal binding properties, Biological Chemistry 2013; vol. 394(6), pp. 761-765.

Wakabayashi et al., Metal ion-independent association of Factor VIII subunits and the roles of calcium and copper ions for cofactor activity and inter-subunit affinity, Biochemistry 2001, vol. 40, 10293-10300.

Wang et al., Coagulation Factor VIII: structure and stability, International Journal of Pharmaceutics, 2003, vol. 259, pp. 1-15.

Winge et al., Development, upscaling and validation of the purification process for human-cl rhFVIII (Nuwiq®), a new generation recombinant factor VIII produced in a human cell-line, Protein Expression and Purification, vol. 115, 2015, pp. 165-175.

\* cited by examiner

METHOD OF SEPARATING FACTOR VIII FROM BLOOD PRODUCTS

FIELD OF THE INVENTION

The present invention pertains to a method for separating Factor VIII from a first composition, in particular a plasma, comprising the Factor VIII protein, and a von-Willebrand-Factor protein and to the method products, i.e. a blood product with reduced amounts of FVIII and/or an FVIII/vWF complex.

BACKGROUND OF THE INVENTION

Hemophilia is a group of hereditary genetic disorders that impair the body's ability to control blood clotting or coagulation. In its most common form, Hemophilia A, clotting factor VIII (FVIII) is deficient, Hemophilia A occurs in about 1 in 5,000-10,000 male births. The FVIII protein is an essential cofactor in blood coagulation with multifunctional properties. The deficiency of FVIII can be treated with plasma-derived concentrates of FVIII or with recombinantly produced FVIII. The treatment with FVIII concentrates has led to a normalized life of the hemophilia patients. Historically, Hemophilia A has been treated with FVIII originating from human blood plasma. In blood plasma, under normal conditions, the FVIII molecule is always associated with its cofactor; von Willebrand factor (vWF), which stabilizes the FVIII molecule from different forms of degeneration.

Many processes have been described for purification of Factor VIII from plasma or cultures which recombinantly produce Factor VIII (rFVIII) with our without the presence of von Willebrand Factor. Commonly, purified FVIII products with low amount of vWF contain added human albumin and or other stabilizers including Calcium ions and increased salt concentration to stabilize the FVIII molecule.

The methods used to purify FVIII from plasma were normally a combination of different precipitation methods such as cryo precipitation, aluminum hydroxide precipitation etc. and chromatography steps mainly ion exchange, affinity and gel filtration steps. In order to improve FVIII products affinity chromatography was employed, which effectively removed contaminants to a high degree of FVIII purity including the possibility to reduce also vWF (Farrugia et al. 1993). In the 90's, the first recombinant FVIII (rFVIII) products were marketed, divided in full length rFVIII molecules, mimicking the main form of FVIII in blood plasma, and B-domain deleted rFVIII molecules (Eriksson et al., 2001), in which one inactive portion (the B-domain) has been removed, both with a high degree of purity (all without vWF). rFVIII is also purified via several purification steps including affinity chromatography such as described in WO 2009/156430 and McCue et al. 2009. These documents disclose the use of an affinity chromatographic step for purification of recombinantly produced Factor VIII (without the presence of von Willebrand Factor), using a non animal derived Fab fragment based affinity resin where the 13 kD ligand binds to the light chain of Factor VIII (see Winge et al, 2015).

Biologically active Factor VIII can be measured with different in vitro analytical methods (FVIII:C), for example FVIII chromogenic assay and/or one stage clot assay (Girma et al., 1998). The chromogenic assay is a two-stage photometric method that measures the biological activity of factor VIII as a cofactor to FIXa. In the method, FX is activated to FXa by FIXa in the presence of calcium ions and phospholipids. Formed FXa cleaves a chromogneic substrate into a product that can be quantified spectrophotometrically. The one-stage clotting assay is based on the ability of a factor VIII containing sample to correct the coagulation time of factor VIII deficient plasma in the presence of phospholipid, contact activator and calcium ions. The time of appearance of a fibrin clot is measured in one step.

For testing rFVIII or purified FVIII samples generally congenital FVIII deficient plasmas are used such as the intrinsic "Factor VIII Deficient Plasma (Congenital)" from Helena Biosciences. However, the availability of these congenital plasmas is limited as it is derived from hemophilia A patients and therefore the quantities of these plasmas are limited. Also FVIII deficient plasmas can be produced by removal of FVIII from normal plasma, i.e. the FVIII/vWF complex from the plasma using antibodies specific for the FVIII/vWF complex, i.e. often an affinity ligand directed against FVIII which is not disturbed by the binding of vWF to FVIII. An example is the Factor VIII Deficient Plasma of Affinity Bioogicals™, Inc.

SUMMARY OF THE INVENTION

The present invention is inter alia based on the surprising finding that a ligand specific for the light chain of FVIII, in particular the Fab fragment based affinity resin sold under the name VIIISelect, under defined conditions efficiently binds to the complex of FVIII and vWF. The present inventors were able to determine specific optimal conditions for the binding.

Thus, according to a first aspect the invention provides a method for separating a FVIII protein from a first composition comprising the FVIII protein, which contains at least the light chain of FVIII, and a vWF protein which comprises at least the FVIII binding domain of vWF, wherein the FVIII protein can form a complex with the vWF protein, the method comprising the steps:

contacting the first composition with an affinity resin comprising a ligand and a matrix, wherein the ligand has an affinity to the light chain of FVIII, and separating the affinity resin from the mixture to obtain a modified first composition and a second composition, wherein the second composition contains the affinity resin, FVIII and a complex of the FVIII protein and the vWF protein.

Importantly, not only FVIII binds to the ligand. The inventors have determined conditions for binding FVIII in complex with vWF and therefore making it possible to separate the FVIII/vWF complex from blood products, in particular plasma. Thus, according to a second aspect the invention provides a method for producing a modified blood product, comprising the steps:

providing a first composition comprising a blood product, in particular a plasma;

performing the separation of FVIII according to the first aspect of the invention; and collecting the modified blood product.

Accordingly, in a third aspect the invention provides a modified plasma obtained by the method according to the second aspect, wherein the concentration of FVIII is less than 4% of the average FVIII concentration of plasma of a healthy human donor.

Modified plasmas with a reduced amount of FVIII, in particular FVIII deficient plasmas, could be useful in the treatment of diseases or disorders such as Disseminated Intravascular Coagulation (DIC) or sepsis. Thus, according to a fourth aspect, the invention provides a modified plasma for use in therapy, wherein the modified plasma is defined according to the third aspect of the invention.

However, an alternative application of the modified blood product according to the third aspect is the application in the analytical testing of FVIII samples. In this regard, according to a fifth aspect the invention provides the use of the modified blood product, in particular a modified plasma according to the third aspect of the invention for testing the concentration and/or activity of FVIII in a sample.

The separation method according to the first aspect is not only useful for separating blood derived FVIII from a blood product sample but instead can also be applied in the purification of FVIII, vWF or the complex thereof.

Thus, according to a sixth aspect the invention provides a method for purifying or enriching an FVIII protein, a vWF protein or a complex of an FVIII protein and a vWF protein comprising the steps:

providing a first composition comprising the FVIII protein, which contains at least the light chain of FVIII, and a vWF protein which comprises at least the FVIII binding domain of vWF, wherein the FVIII protein can form a complex with the vWF protein, performing the separation method according to the first aspect;

optionally applying at least one washing step to the second composition, wherein the second composition contains the affinity resin and a complex of the FVIII protein and the vWF protein; and optionally eluting a third composition comprising vWF, in particular with an elution buffer comprising $CaCl_2$); and eluting a fourth composition comprising a complex of the FVIII protein and the vWF protein or the FVIII protein from the affinity resin.

Finally, according to a seventh aspect the invention provides a composition comprising a complex of a FVIII protein and a vWF protein or a purified FVIII protein, or a purified vWF protein, obtained by the method according to the sixth aspect.

DETAILED DESCRIPTION OF THE INVENTION

Figure 1:
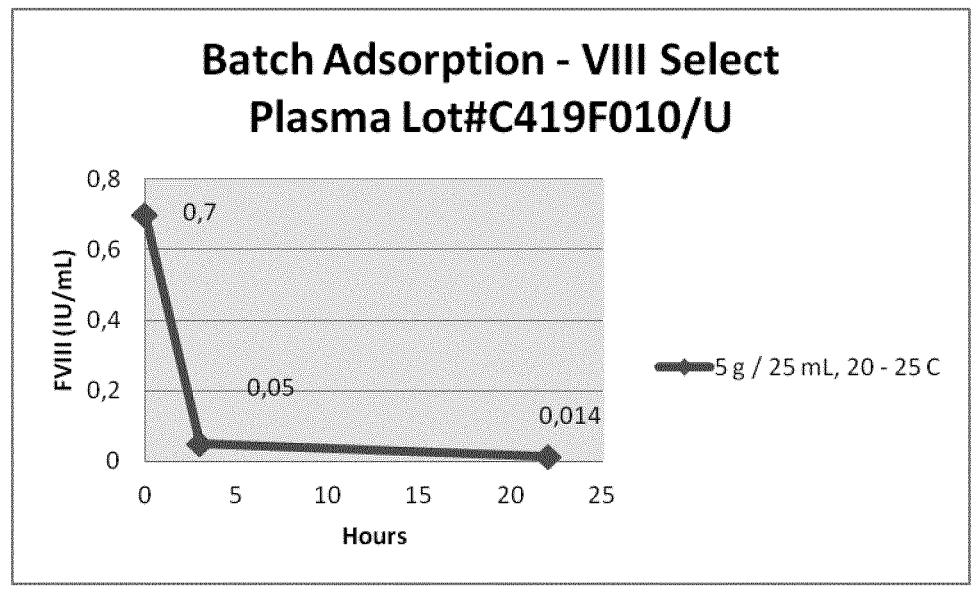
FIG. 1 shows a diagram of batch adsorption were the concentration of FVIII in plasma after different incubation times with the affinity resin VIIISelect, is measured. The FVIII concentration is shown on the Y-axis, the time on the X-axis. FVIII concentration in the plasma sample was measured before mixing of the plasma with VIIISelect, after four hours and after 24 hours. The legend of the diagram shows the ratio of VIIISelect material in gram and volume of the plasma in ml. The indicated temperature (20-25° C.) shows the incubation temperature.

The inventors have developed a novel method for binding a FVIII protein in the presence of vWF and therefore separating a complex of a FVIII protein and a vWF protein using a ligand that is specific for the light chain of FVIII. This is surprising because the vWF is known to bind to the light chain of FVIII (see for example Wang et al. 2003, at page 5, left column or and Chiu et al., 2015) and should therefore prevent light chain specific ligands of FVIII from binding to FVIII when in complex with vWF. Thus the present invention provides additional options for the purification the FVIII/vWF complex. Moreover, with determining optional conditions for the binding of plasma derived FVIII/vWF complexes, the invention provides a suitable method for producing FVIII deficient plasmas.

According to a first aspect the invention provides a method for separating a FVIII protein from a first composition comprising the FVIII protein, which contains at least the light chain of FVIII, and a vWF protein which comprises at least the FVIII binding domain of vWF, wherein the FVIII protein can form a complex with the vWF protein, the method comprising the steps:

contacting the first composition with an affinity resin comprising a ligand and a matrix, wherein the ligand has an affinity to the light chain of FVIII, and separating the affinity resin from the mixture to obtain a modified first composition and a second composition, wherein the second composition contains the affinity resin, FVIII and a complex of the FVIII protein and the vWF protein.

The FVIII protein according to the invention may be human or animal full length Factor VIII and any fragment, mutant or variant thereof. The FVIII protein may be plasma derived or recombinant. Further, the FVIII protein may be glycosylated or unglycosylated. Factor VIII in humans is coded by the F8 gene which comprises 187.000 base pairs in six axons. The transcribed mRNA has a length of 9.029 base pairs and is translated to a protein with 2.351 amino acids from which by a posttranslational modification 19 amino acids are removed. The FVIII molecule in humans is glycosylated on a 31 amino acid side chain (25×N-glycosylation, 6×O-glycosylation).

After translation the amino acid chain is cleaved by specific proteases onto positions leading to the formation of a heavy chain with about 200 kDa and a light chain with about 80 kDa. The domain organization is typically characterized as A1-A2-B-A3-C1-C2. The light chain is a made-up of domains A3-C1-C2. The heavy chain is in principal composed of the domains A1-A2-B. Heavy chains found in plasma have a heterogeneous composition with molecular weights varying from 90 to 200 kDa. The reason for this are the heterogeneity in its glycosylation, the existence of splice variants and existence of proteolytic products such the B domain depleted heavy chain $A_1$ $A_2$. The amino acid sequence of the full length FVIII is identified by amino acids 20 to 2.351 of P00451 of SwisProt, Jul. 21, 1986. The FVIII protein in particular has an amino acid sequence with a sequence identity to amino acids 20 to 2351 of P00451 of SwissProt of Jul. 21, 1986 of at least 80%, 85%, 90%, 95%, 98%, 99% or 100%. Preferably the sequence homology to the amino acid sequence defined by amino acids 20 to 2351 of P00451 is at least 95%

The exact conditions of the heavy and the light chain association are not in detail known, but articles suggest the involvement of a metal ion bridge which together with hydrophobic interactions is forming and holding together the complex.

Different metal ions have been suggested to take part in the interaction, including calcium, copper, zink, manganese etc. (Wang et al. 2003). For a recently developed B-domain deleted recombinant Factor VIII product, it was stated that the molecule contained three metal ions; calcium, copper and zink (Svensson et al.).

The method for separating according to the invention leads to the separation of the FVIII protein from the first composition. As the vWF protein is also present in the sample and comprises the FVIII binding domain of vWF at least a part of the FVIII protein present in the first composition will be in form of a complex with a vWF protein.

According to one embodiment of the first aspect the first composition comprises a blood product. The method according to the invention can be used to lower the concentration of FVIII in blood products or remove the FVIII from the blood product.

As used herein "blood product" refers to whole blood of a mammal or subsets of whole blood, in particular plasma, serum or further subsets of plasma and serum.

As used herein a "modified blood product" is a blood product underwent a further processing step, such as a precipitation step especially a cold precipitation step, virus inactivation, chemical or heat treatment or/and removal of specific components. Accordingly modified plasma is obtained by processing plasma. Modified whole blood is obtained by a further processing step on whole blood.

"Plasma" as used herein refers to the blood plasma of mammals. It is a pale white, sometimes yellow, liquid component of blood that normally holds the blood cells in whole blood in suspension. Plasma is mostly water and contains dissolved proteins, glucose, clotting factors, electrolytes, hormones, and carbon dioxide. Plasma can be prepared from blood, for example by centrifugation of fresh blood containing an anticoagulant in which the blood cells moved to the bottom of the centrifugation tube. The supernatant of this process is blood plasma.

"Subset of whole blood" as used herein refers to a solution of suspension derived from whole blood comprising a part of the components of whole blood.

"Coagulation factor" as used herein refers to proteins naturally occurring in the blood that are part of the coagulation cascade, such as fibrinogen, prothrombin, Factor VII, Factor IX or Factor VIII.

"Cryoprecipitate" as used herein is a blood product prepared from plasma. To acquire cryoprecipitate, the plasma, normally frozen, is temperated to approximately 0 degree Celcius followed by a centrifugation and the collection of the precipitate.

The term "cryosupernatant" as used herein refers to plasma from which the cryoprecipitate has been removed. The resulting plasma has reduced levels, but still considerable amounts, of FVIII, vWF, FXIII, fibronectin and fibrinogen.

According to one embodiment the FVIII protein is selected from human plasma derived FVIII, an FVIII derivative naturally occurring in blood, in particular an FVIII derivative naturally occurring in human blood, recombinant human full length FVIII and recombinant human B domain depleted FVIII. According to a preferred embodiment the FVIII protein is human plasma derived FVIII. Human plasma derived FVIII is in particular the full length FVIII including all sub-domains A1, A2, B, A3, C1 and C2. This is in particular relevant if the method for separating according to the first aspect is used with a blood product as first composition. Thus, accordingly the FVIII protein may be any FVIII derivative naturally occurring in blood, in particular including the full length FVIII and human B domain depleted FVIII. Alternatively, the method for separating the FVIII protein can be used with a recombinantly produced FVIII protein. A recombinantly produced FVIII protein may be a FVIII with the amino acid sequence of human full length FVIII. Alternatively, the recombinant FVIII protein may be a recombinant human B domain depleted FVIII.

"FVIII light chain" as used herein relates to a part of Factor VIII. The FVIII light chain in particular has an amino acid sequence with a sequence homology to amino acids 1668 to 2351 of P00451 of SwissProt of Jul. 21, 1986 of at least 80%, 85%, 90%, 95%, 98%, 99% or 100%. Preferably the sequence homology to the amino acid sequence defined by amino acids 1668 to 2351 of P00451 is at least 95%

Recombinant FVIII proteins include FVIII fusion proteins such as FVIII albumin fusion proteins as described in Oldenburg et al., 2014 and/or FVIII FC fusion proteins.

Recombinant FVIII proteins according to the invention can be produced in any known recombinant expression system including, but not limited to, yeast expression systems, Baculovirus/insect cell expressions systems, mammalian expressions systems such as CHO or BHK and in human cell lines such as HEK293F cells. Recombinant FVIII proteins expressed in human cell lines are preferred as they mimic the human glycosylation pattern.

The vWF protein according to the invention maybe human or animal full length vWF and any fragment, mutant or variant thereof. vWF is a multimeric adhesive glycoprotein present in the plasma of mammals, which has multiple physiological functions. During primary hemostasis, vWF acts as a mediator between specific receptors on the platelet surface and components of the extracellular matrix such as collagen. Moreover, vWF serves as a carrier and stabilizing protein for procoagulant Factor VIII. VWF is synthesized in endothelial cells and megakaryocytes as a 2813 amino acid precursor molecule. The precursor polypeptide, pre-pro-vWF, consists of a 22-residue signal peptide, a 741-residue pro-peptide and the 2050-residue polypeptide found in mature plasma Von Willebrand Factor (Fischer et al., 1994). Full length vWF is identified by Uniprot entry P04275.

Upon secretion into plasma, vWF circulates in the form of various species with different molecular sizes. These vWF molecules consist of oligo- and multimers of the mature subunit of 2050 amino acid residues. vWF can be usually found in plasma as multimers ranging in size approximately from 500 to 20.000 kDa (Furlan et al. 1996). According to one embodiment the vWF protein is a plasma derived vWF multimer. According to one embodiment the vWF protein is a plasma derived vWF monomer. The vWF in particular has an amino acid sequence any of the sequences of Uniprot entry P04275 of at least 80%, 85%, 90%, 95%, 98%, 99% or 100%.

Recombinant vWF proteins according to the invention can be produced in any known recombinant expression system including, but not limited to, yeast expression systems, Baculovirus/insect cell expressions systems, mammalian expressions systems such as CHO or BHK and in human cell lines such as HEK293F cells. Recombinant vWF proteins expressed in human cell lines are preferred as they mimic the human glycosylation pattern.

The ligand according to the invention can be any molecule or entity that has an affinity to the light chain of FVIII. As used herein "affinity" relates to the property of specifically binding to a target, here the light chain of FVIII. The binding of the ligand to FVIII may be covalent or non-covalent, reversible or irreversible. Preferably, the binding is non-covalent and reversible. According to one embodiment the ligand is a polypeptide with an affinity to the light chain of FVIII.

A "peptide" as used herein may be composed of any number of amino acids of any type, preferably naturally occurring amino acids, which, preferably, are linked by peptide bonds. In particular, a peptide comprises at least 3 amino acids, preferably at least 5, at least 7, at least 9, at least 12, or at least 15 amino acids. Furthermore, there is no upper limit for the length of a peptide. However, preferably, a peptide according to the invention does not exceed a length of 500 amino acids, more preferably it does not exceed a length of 300 amino acids; even more preferably it is not longer than 250 amino acids.

Thus, the term "peptide" includes "oligopeptides", which usually refer to peptides with a length of 2 to 10 amino acids, and "polypeptides" which usually refer to peptides with a length of more than 10 amino acids.

The term "protein" refers to a peptide with at least 60, at least 80, preferably at least 100 amino acids.

The term "fusion protein" according to the invention relates to proteins created through the joining of two or more genes, cDNAs or sequences that originally coded for separate proteins/peptides. The genes may be naturally occurring in the same organism or different organisms or may be synthetic polynucleotides.

The relatedness between two amino acid sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using thenobrief option) is used as the percent identity and is calculated as follows:

(Identical Residues×100)/(Length of Alignment−
Total Number of Gaps in Alignment)

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim, except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" limits the scope of a claim to the specified materials or steps "and those that do not materially affect the basic and novel characteristic(s)" of the claimed invention. "A 'consisting essentially of' claim occupies a middle ground between closed claims that are written in a 'consisting of' format and fully open claims that are drafted in a 'comprising' format."

An "affinity resin" as used herein is a chromatography medium with an affinity to a specific protein. The affinity resin comprises at least a matrix and a ligand with an affinity to a protein.

A "matrix" as used herein is a substance usually in bead form to which a specific ligand is covalently bound. A matrix according to the invention should be
- insoluble in solvents and buffers employed in the process;
- chemically and mechanically stable; and
- easily coupled to a ligand or spacer arm onto which the ligand can be attached.

Additionally it should exhibit good flow properties and have a relatively large surface area for attachment. Preferably, a matrix is made of agarose, glass, cellulose or polyacrylimide. According to a one embodiment the matrix is a highly cross linked agarose.

As shown in the examples the VIIISelect allows an efficient binding of FVIII in the presence of the vWF protein and/or the FVIII/vWF complex. VIIISelect is based on a highly cross-linked agarose base matrix. This agarose base matrix is bound to a 13 kDa Fab fragment which specifically binds to the light chain of FVIII. The 13 kDa Fab fragment is connected to the agarose matrix via a hydrophilic spacer. Accordingly, the ligand according to the invention is preferably a recombinant polypeptide. According to one embodiment the size of the ligand is in the range from 2 to 50 kDa. Preferably the molecular weight of the polypeptide ligand is in the range from 5 to 30 kDa, more preferably in the range from 10 to 20 kDa. A size above 30 kDa is likely to lead to sterical hindrance due to the presence of the vWF on the light chain of FVIII. The molecular weight of less than 5 kDa can have the disadvantage of being less specific in its binding to the target molecule.

According to a preferred embodiment the polypeptide is an antibody Fab fragment. Fab is the antigen binding fragment of an antibody. Antibodies and antibody fragment exhibit particularly high-binding affinities to their binding targets, i.e. antigens. Thus, a Fab fragment is a preferred ligand for the separation of FVIII. The polypeptide, in particular the Fab fragment, is preferably a recombinant polypeptide produced in a non-animal source. Production in a non-animal source has the advantage that the risk of the presence of viruses or other toxins potentially problematic for the patient is minimized. According to a preferred embodiment the ligand is a recombinant polypeptide produced in yeast cells.

According to one embodiment the ligand is coupled to the resin via a spacer. A spacer arm according to the invention is chosen so that it improves the binding probability of the ligand to the FVIII light chain. In particular the spacer should have a length to reduce steric hindrance of the binding between the ligand and the FVIII light chain by the matrix. According to a preferred embodiment the spacer is represented by the following structure:

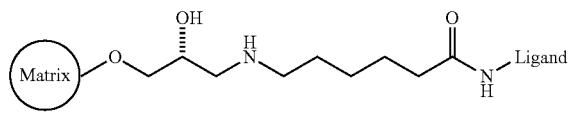

According to one embodiment the spacer is a hydrophilic compound. The matrix is preferably in the form of porous beads. According to a preferred embodiment the resin coupled ligand is defined as VIIISelect. VIIISelect is an affinity purification resin commercially available from GE Healthcare (data file 28-9662-37 AB, GE healthcare). The capacity is generally 20 000 IU/ml gel. The long term pH stability of VIIISelect is given at pH 3-10 short term stability at pH 2-12, which can be used for the regeneration of the affinity resin to be able to perform repeated purifications on the VIIISelect affinity resin.

The affinity resin is preferably prepared before the contacting the first composition by application of different buffers. For equilibration the affinity resin is preferably treated with one or more of the following buffers: regeneration buffer, a wash buffer, an elution buffer, and/or an equilibration buffer.

The affinity resin may be treated with a wash buffer followed by the equilibration buffer. In particular affinity resins that were not used before may be treated this way. Affinity resins that were used before may preferably be treated with the elution buffer, the regeneration buffer and the equilibration buffer in that order.

The regeneration buffer preferably comprises HAc, more preferably HAc in a concentration of 0.1 M. The wash buffer preferably comprises NaCl, more preferably at a concentration of 0.5-1 M. Preferably, concentration of $CaCl_2$) in the wash buffer is at most 50 mM. More preferably the wash buffer does not contain calcium, in particular $CaCl_2$) when to produce FVIII deficient plasma. The elution buffer preferably comprises 50% ethylene glycol or 50% propylene glycol or 2 M of $MgCl_2$. The pH is preferably in the range from 6.2 to 6.8 more preferably in the range from 6.4-6.6.

Preferably, the concentration of $CaCl_2$) in the elution buffer is at most 50 mM. The equilibration buffer comprises preferably NaCl and Na-Citrate. Preferably, concentration of $CaCl_2$) in the equilibration buffer is at most 50 mM. More preferably the equilibration buffer does not contain calcium, in particular $CaCl_2$) when to produce FVIII deficient plasma. All buffers can in addition contain; imidazol, histidine, sodium phosphate, sodium citrate, Tris, HEPES, glycine, NaCl and Tween80. More preferably the equilibration buffer comprises 30 g/kg NaCl and 6.0 g/kg Na-Citrate at a pH of pH 6.4-6.6. The affinity resin is preferably stored in ethanol, preferably in 20% ethanol.

The separating step according to the invention can be performed continuously in a column or in batch form. As shown in the examples both batch separation and affinity chromatography lead to a separation of the FVIII from the sample.

However, by a continuous column chromatography comparable or even better separation results were obtained in shorter time. Thus, according to a preferred embodiment the separating is performed continuous, i.e. in form of a column chromatography.

According to one embodiment the resin coupled ligand is provided in a column forming a resin bed for contacting the first composition. According to one embodiment the bed height of the resin is at least 2 cm. With a height of less than 2 cm, the contact time/flow rate would be low and the process time to high and therefore the binding capacity of the resin bound ligand would be too low per time unit. Preferably, the bed height of the affinity resin is at least 5 cm or more preferably at least 10 cm and in particular at least 20 cm. The higher the bed height the longer contact time at the same flow rate and the higher binding capacity per time unit. However with the bead height also the back pressure increases. Thus, bead height is preferably chosen such that the back pressure does not exceed the maximum of 0.3 MPa. A backpressure above 0.3 MPa may lead to a collapse of the column material Generally, for affinity chromatography a high flow rate is preferred as it minimizes the time for the process step. However, as shown in the example the flow rate has a large impact on the efficiency of the separation. In the column chromatography the flow rates of the first and modified first composition are identical. The first composition is the starting material, and comprises in particular a blood product including FVIII and vWF. The modified first composition is the affinity chromatography flow-through obtained after contacting the first composition with the affinity resin.

According to one embodiment the flow rate of the first composition is equal to or below 30 cm/h. The flow rate over the column is determined by the volumetric flow rate in L/h which is equal to the flow velocity in cm/h of the mobile phase over the column. The following formula is defining the relationship:

Volumetric flow rate (L/h)=Flow velocity (cm/h) multiplied with the column cross-sectional area ($cm^2$) divided with 1000

A flow rate of 30 cm/h or less leads to a separation of FVIII from the first composition. A flow rate of 15 cm/h or less leads to a strongly reduced concentration of FVIII in the third composition. Thus, according to one embodiment, the flow rate is equal to or below 15 cm/h. For complete removal of FVIII from a plasma as shown in the example a flow rate equal to or below 10 cm/h is required. Thus, according to one embodiment the flow rate is equal to or below 10 cm/h. According to a further embodiment the flow rate is equal to or below 7.5 cm/h.

According to one embodiment the concentration of the FVIII protein in the first composition is equal to or below 1 IU/mL. As shown in the examples the efficiency of separation of FVIII, in particular of the FVIII/vWF complex, can be dependent on the concentration of FVIII in the first composition, in particular in the blood product.

From the experiments it is shown that the concentration of FVIII in this composition may be equal to or below 1 IU/mL. A concentration of 1 IU/mL is the normal concentration of FVIII in the blood of a healthy individual. According to one embodiment another concentration of the FVIII protein and the first composition is equal to or below 0.7 IU/mL. According to one embodiment the concentration is equal to or below 0.4 IU/mL. For a complete removal of FVIII from the first composition the concentration of the FVIII protein in the first composition is preferably equal to or below 0.2 IU/mL. A complete removal is defined as a concentration below 0.01 IU/mL. A plasma with a concentration below 0.01 IU/mL is referred to as "FVIII deficient plasma".

The concentration of the FVIII protein in a sample is given as the FVIII activity/volume.

As shown in the examples the ratio of the volume of the first composition to the volume of the affinity resin has an influence on the efficiency of the separation of the FVIII protein from the first composition. The volume of the affinity resin is determined by removing the liquid environment of the resin, by for example suction over a filter membrane retaining the resin, and measuring the remaining resin volume. Generally, in particular for agarose matrix based resins, the density of the affinity resin is about 1 g/ml. Accordingly, the volume of the affinity resin is proportional to the amount of matrix in the affinity resin and thus to the ligand bound to the matrix. According to one embodiment the volume of the first composition to the volume of the affinity resin is in the range from 5:1 to 100:1. A concentration of 100:1 is likely to exceed the maximum loading capacity of the affinity resin and, thus, leading to a less efficient separation of the FVIII protein from the first composition. Below a concentration of 5:1 the separation procedure is not time and cost efficient as only little amounts of product could be produced at a time per amount of affinity resin.

Preferably, the ratio of the volume of the first composition to the volume of the affinity resin is in the range from 10:1 to 70:1. Thus according to one embodiment the ratio of the volume of the first composition to the volume of the affinity resin is in the range from 10:1 to 50:1. Based on the examples it is shown that in particular the defined experimental setup concentration of 50:1 should not be exceeded in order to obtain an efficient FVIII reduction in the first composition.

Experimental data provided in the experiments show that in the chosen experimental setup, is the ratio of the first composition to the volume of the affinity resin should be in the range from 20:1 to 40:1 in order to provide a sufficient yield of FVIII deficient plasma. Thus, according to a preferred embodiment the ratio of the volume of the first composition to the volume of the affinity resin is in the range from 20:1 to 40:1.

The inventors have additionally identified that the contact time is a relevant parameter for the efficiency of the separation method. This was found for both the batch and the continuous separation method. For the continuous separation the contact time is dependent on the flow rate and the size, in particular the length, the diameter of the column and thus the volume of the affinity resin bead. In order to obtain a significant reduction of the FVIII/vWF complex in the first composition, the contact time of the first composition and the affinity agent is at least 5 min. According to one embodiment the contact time of the first composition and the affinity agent is at least 10 min. For removal of the FVIII/vWF complex from a plasma, i.e. obtaining a concentration of below 0.01 IU/mL of FVIII, the contact time should be at least 20 min. Preferably the contact time is at least 30 min.

In case the separation is performed in batch form during continuously gentle mixing using for example a wave board with a frequence of approximately 10-50 waves/minute or other similar mixing device, a contact time of at least 4 h leads to a significant decrease of FVIII in the first composition. According to one embodiment the separating is performed in batch form and the contact time of the first composition and the affinity resin is at least 12 h. More preferably, the contact time is at least 24 h. With a contact time of 24 h it was possible to reduce the concentration below the 0.01 IU/mL FVIII activity.

According to one embodiment the number of vWF protein monomers/multimers in the first composition is higher than the number of FVIII protein monomers. Thus, even if FVIII is completely removed from the first composition, the main part of vWF will be left in the first composition even after FVIII removal. However, the removed FVIII will still bind some of the vWF molecules but due to the big difference in initial concentration of FVIII and vWF (generally in human blood the ratio of vWF to FVIII is about 50:1) the decrease of vWF in the first composition will not be big.

According to one embodiment the ratio of the vWF protein to the FVIII protein is at least 1:5. Preferably the ratio of the vWF protein to the FVIII protein is at least 10:1. More preferably the ratio of the vWF protein to the FVIII protein in the first composition is at least 20:1. According to one embodiment the ratio of the vWF protein monomers to the FVIII protein is at least 50:1. vWF is in generally present in human blood in the form of multimers. Therefore one FVIII protein might bind to more than one vWF. Accordingly, in order to keep sufficient amount of vWF while depleting FVIII from a blood product it is necessary to have a high ratio of vWF protein to FVIII protein.

As shown in the examples the binding efficiency of the ligand to FVIII, i.e. the reduction of FVIII activity in the modified first composition—the modified plasma—after affinity purification is improved at higher temperatures. Thus, preferably the temperature during the contacting step of the first composition and the affinity resin is above 4° C. More preferably the temperature is above 15° C. As shown, good results in separating FVIII from the first composition were achieved by a temperature in the range from 20 to 25° C. Due to stability considerations, the temperature is preferably not above 37° C. According to one embodiment of the method the temperature during the contacting step is above 20° C.

According to one embodiment the first composition comprises a blood product. The first composition may also consist of a blood product. The blood product can be selected from whole blood or blood products, plasma or serum. According to a preferred embodiment the blood product is a human blood product. According to one embodiment the first composition further comprises a buffer. The buffer substances may be selected from HEPES, MES, sodium acetate, sodium phosphate and histidine, lysine and arginine. The buffer in particular buffers in a pH range of 6-8. According to one embodiment the buffer is HEPES. The HEPES may for example be present in the first composition in a concentration in the range from 0.001 g/mL to 0.1 g/mL based on the total volume of the first composition, preferably in the range from 0.005 g/mL to 0.05 g/mL, more preferably in the about 0.01 g/mL at a pH between 6.5-7.5.

According to one embodiment the blood product is a plasma, in particular plasma from a human. The plasma can be pre-treated plasma or a virus-inactivated plasma. Pre-treated plasmas include cryoprecipitate and cryosupernatant. The cryosupernatant and cryoprecipitate are preferably obtained by freezing fresh plasma and thawing it at a temperature of about 0° C. which leads to a precipitation. The precipitate is cryoprecipitate the supernatant is termed cryosupernatant. The plasma is most preferably a cryosupernatant.

The virus-inactivated plasma is in particular a chemically virus-inactivated plasma. An example of virus-inactivated plasma is the plasma sold under the trade name "Octaplas™".

The separation method according to the invention may not only be used for changing the concentration of FVIII in human blood or plasma, in particular removing FVIII from the plasma, but also as a step in the purification of the recombinant complex. Thus, according to an alternative embodiment the FVIII protein or the vWF protein is a recombinantly expressed protein. According to a preferred embodiment the FVIII protein and the vWF protein are both recombinantly expressed proteins. In case of the recombinant expression, the vWF protein may in particular be a specific sub-domain of human vWF. The sub-domain of vWF preferably has an amino acid sequence with a sequence homology to the amino acid sequence defined by amino acids 764 to 1035 of P04275-1 of at least 80%, 85%, 90%, 95%, 98%, 99% or 100%. Preferably the sequence homology is at least 95%.

The method of separation according to the first aspect is in particular used for producing a modified blood product, in particular an FVIII deficient blood product. Thus according to a second aspect the invention provides a method for producing a modified blood product, comprising the steps of:
 providing the first composition comprising a blood product;
 performing a separation method according to the first aspect; and
 collecting the modified blood product.

The blood product in this regard in preferably a plasma and thus the modified blood product is preferably a modified plasma. The modified blood product is more preferably an FVIII deficient blood product, in particular an FVIII deficient plasma.

The method according to the second aspect can be directly combined with the production of a plasma in order to obtain a modified plasma, in particular an FVIII deficient plasma. Thus according to one embodiment of the second aspect the method comprises one or more of the following steps:
 providing a whole blood sample;
 removing of blood cells from the whole blood by centrifugation and/or filtration to obtain a blood plasma;
 freezing of the blood plasma
 optionally storing the frozen blood plasma;
 thawing the frozen blood plasma to around 0° C. causing protein precipitation;
 removing the protein precipitate from the frozen blood plasma by centrifugation and/or filtration to obtain a cryo-precipitated plasma; and
 optionally freezing, storing and thawing the cryo-supernatant before the next step in the process According to an alternative embodiment the method of the second aspect further comprises all of the following steps:
 providing a whole blood sample;
 removing of blood cells from the whole blood by centrifugation and/or filtration to obtain a blood plasma;
 freezing of the blood plasma
 optionally storing the frozen blood plasma;
 thawing the frozen blood plasma to around 0° C. causing protein precipitation;
 removing the protein precipitate from the frozen blood plasma by centrifugation and/or filtration to obtain a cryo-supernatant; and
 optionally freezing, storing and thawing the cryo-supernatant before the next step in the process.

According to one embodiment the method comprises one or more of the steps:
 providing a whole blood sample;
 removing of blood cells from the whole blood by centrifugation and/or filtration to obtain a blood plasma;
 freezing of the blood plasma;
 optionally storing the frozen blood plasma;
 thawing the frozen blood plasma to a temperature in the range of around to 10-25° C.;
 performing a chemical treatment to obtain a chemically treated plasma;
 removing of the virus inactivation chemicals, in particular by oil extraction and hydrophobic interaction chromatography to obtain a virus inactivated plasma and
 optionally freezing, storing and thawing the virus inactivated plasma before the next step in the process.

According to one embodiment the method comprises all of the steps:
 providing a whole blood sample;
 removing of blood cells from the whole blood by centrifugation and/or filtration to obtain a blood plasma;
 freezing of the blood plasma;
 optionally storing the frozen blood plasma;
 thawing the frozen blood plasma to a temperature in the range of around to 10-25° C.;
 performing a chemical treatment to obtain a chemically treated plasma;
 removing of the virus inactivation chemicals, in particular by oil extraction and hydrophobic interaction chromatography to obtain a virus inactivated plasma;
 optionally freezing, storing and thawing the virus inactivated plasma before the next step in the process.

The chemical treatment is preferably performed by adding 1% TNBP and 1% Triton X-100 and gently stirring for at least 30 minutes.

For certain uses it may be beneficial to add exogenous vWF protein to the blood product, in particular the plasma. Exogenous vWF according to the invention is vWF not derived from the the blood product. Exogenous vWF can be plasma derived or recombinant vWF. The process of adding vWF to the blood product is referred to as spiking. Spiking vWF may be necessary in order to restore natural concentration values of vWF in the modified plasma in which during the process both FVIII to a concentration of less than 0.01 IU/mL and vWF in the plasma is significantly removed.

With the method according to the second aspect, it is possible to produce a modified plasma with highly reduced levels of FVIII. According to one embodiment a modified plasma obtained by a method according to the second aspect has a concentration of FVIII that is less than 4% of the average FVIII concentration of plasma of a healthy donor. The plasma of a healthy donor generally contains a concentration of the plasma of a healthy donor generally contains a concentration of FVIII of about 1 IU/mL. For several applications it is maybe desired to provide a plasma with an even lower concentration of FVIII. Thus according to one embodiment the concentration of FVIII is less than 3% of the average FVIII concentration of plasma of a healthy donor. According to a further embodiment the FVIII concentration is less than 2% of the average FVIII concentration of plasma of a healthy donor. As defined above a modified plasma is defined as FVIII deficient if it contains less than 1% of the concentration of a healthy donor, namely in about 0.01 IU/mL.

As blood—in particular human blood—and therefore also plasma derived from the blood, contains a higher amount of vWF then of FVIII, the vWF is not completely depleted. For example, the modified plasma may be used for testing plasma derived or recombinant FVIII samples. For this the plasma must contain all clotting factors besides FVIII, in particular a modified blood product contains a sufficient concentration of vWF. Preferably, the concentration of vWF is at least 20% of the average vWF concentration of plasma of a healthy human donor. More preferably the concentration of vWF is at least 30% of the average vWF concentration of plasma of a healthy human donor. The concentration of the vWF in the modified plasma may also be at least 40% of the average vWF concentration of plasma of a healthy human donor. According to a preferred embodiment the concentration of vWF is at least 50% of the average vWF concentration of plasma of a healthy human donor. With a concentration of 50% of the concentration of a healthy human donor the vWF concentration should be sufficient for FVIII tests.

However, higher concentrations of vWF can be required in the modified plasma due to different reasons, for example during FVIII analysis to increase the stability environment for the FVIII product and/or due to the use of the modified plasma in different specific therapies requiring higher vWF amounts. Thus, by spiking the modified plasma with exogenous vWF, recombinant or plasma derived vWF the modified plasma may be obtained to the vWF concentration of at leas 75% of the average vWF concentration of plasma of a healthy human donor, preferably at least 85%, more preferably at least 90%, in particular at least about 100%. For use of the plasma in analytical methods for detecting FVIII and for specific therapies the concentration of FVIII is in particular below 0.01 IU/mL, i.e. 1% of the FVIII concentration of plasma of a healthy human donor and the vWF concentration is at least 90% of the vWF concentration of plasma of a healthy human donor. The method according to the second aspect for making a modified plasma, in particular a plasma with reduced FVIII content preferably does not lead to a significant decrease of fibrinogen in the modified plasma.

According to one embodiment of the modified plasma according to the third aspect the concentration of fibrinogen is at least 1 g/ml based on the volume of a modified plasma, preferably at least 1.3 g/ml, more preferably 1.5 g/ml. The FX activity of the modified plasma is preferably at least 0.5 IU/mL, more preferably in the range of 0.9-1.1 IU/mL. The modified plasma should preferably have a low amidolytic activity. The amidolytic activity can for example be based on the protease substrate S-2288 or S-2366. The amidolytic activity based on S-2288 substrate is determined as shown in Example 4. Based on the determination method shown in Example 4 the amidolytic activity with respect to S-2288 is preferably equal to or below 1 mOD/min, more preferably equal to or below 0.5 mOD/min, in particular preferably equal to or below 0.2 mOD/min. Further, based on the determination method shown in Example 4 the amidolytic activity with respect to S-2366 is equal to or below 0.5 mOD/min, preferably equal to or below 0.2 mOD/min, more preferably equal to or below 0.1 mOD/min.

As discussed above there are several uses for a modified plasma according to the third aspect. In particular the modified plasma can be used in therapies. Thus, according to a fourth aspect, the invention provides a modified plasma for use in therapy. An example for use of the modified plasma is the treatment of disorders which require a decreased coagulation activity. This may be in particular situations during disseminated intravascular coagulation (DIC). DIC is a pathological process characterized by the widespread activation of the clotting cascade that results in formation of blood clots in small vessels throughout the body. This leads to compromise of tissue blood flow and can ultimately lead to multiple organ damage. Administration of FVIII deficient plasma leads to a dilution of FVIII and addition of protease inhibitors like antithrombin, protein C, protein S etc. which as well can have an anti-inflammatory effect and therefore in combination with a reduced clotting activity a better ability for the body to control the DIC situation.

Sepsis is in many occasions a pre-phase of DIC. Thus, also during some occasions it could be advantageous to dilute the FVIII concentration and add fresh amounts of protease inhibitors/anti-inflammatory substances during treatment of sepsis, for prophylactic reasons to further mimic the risk of developing DIC.

Alternatively the modified plasma with reduced FVIII concentration may be used for the testing of the concentration and/or activity of FVIII in a sample in an analytical method. Thus according to a fifth embodiment the invention provides the use of the modified plasma according to the third embodiment for testing of the concentration and/or the activity of FVIII in a sample. For full length FVIII and functional derivatives thereof the activity is a direct measure of the concentration and is generally used to determine the concentration. The activity and the concentration FVIII relate in the following way: 1 IU/mL is equivalent to a concentration of 0.1 µg/mL B-domain depleted FVIII and approximately a factor 2 higher for full length FVIII.

With the method according to the invention it is not only possible to remove or reduce the concentration of FVIII in a sample. As shown the examples with an FVIII affinity to the light chain also binds to a complex of the FVIII protein and the vWF protein.

Thus, according to a sixth aspect the invention provides a method of purifying and/or enriching a FVIII protein, a vWF protein or a complex of an FVIII protein and a vWF protein, comprising the steps:
  providing a first composition comprising the FVIII protein, which contains at least the light chain of FVIII, and a vWF protein which comprises at least the FVIII binding domain of vWF, wherein the FVIII protein can form a complex with the vWF protein,
  performing the separation method according to the first aspect;
  optionally applying at least one washing step to the second composition, wherein the second composition contains the affinity resin and a complex of the FVIII protein and the vWF protein; and
  optionally eluting a third composition comprising vWF, in particular with an elution buffer comprising $CaCl_2$); and eluting a fourth composition comprising a complex of the FVIII protein and the vWF protein or only the FVIII protein from the affinity resin.

According to one embodiment of the sixth aspect the method is for purifying and/or enriching a complex of an FVIII protein and a vWF protein and comprises the steps:
providing a first composition comprising the FVIII protein, which contains at least the light chain of FVIII, and a vWF protein which comprises at least the FVIII binding domain of vWF, wherein the FVIII protein can form a complex with the vWF protein,
performing the separation method according to first aspect;
optionally applying at least one washing step to the second composition, wherein the second composition contains the affinity resin and a complex of the FVIII protein and the vWF protein; and
eluting a fourth composition comprising a complex of the FVIII protein and the vWF protein from the affinity resin.

According to one embodiment of the sixth aspect the method is for purifying and/or enriching an FVIII protein and comprises the steps:
providing a first composition comprising the FVIII protein, which contains at least the light chain of FVIII, and a vWF protein which comprises at least the FVIII binding domain of vWF, wherein the FVIII protein can form a complex with the vWF protein;
performing the separation method according to the first aspect;
optionally applying at least one washing step to the second composition, wherein the second composition contains the affinity resin and a complex of the FVIII protein and the vWF protein;
eluting a fourth composition comprising the vWF protein from the affinity resin; and
eluting a fifth composition comprising the FVIII protein from the affinity resin.

According to one embodiment the affinity resin is equilibrated before contacting the first composition with an equilibration buffer. The equilibration buffer preferably is selected from imidazol, histidine, sodium phosphate, sodium citrate, Tris, HEPES, glycine, NaCl and Tween80 Preferably, the pH of the equilibration buffer is in the range of 6.9 to 7.8, preferably in the range from 7.2 to 7.6. According to one embodiment the concentration of imidazol is about 10 mM, the concentration of glycine is about 0.5 to 1%, the concentration of NaCl is about 0.1 M and the concentration of Tween is about 0.02%. Preferably the pH is about 7.4. Preferably, concentration of $CaCl_2$) in the equilibration buffer is at most 50 mM. More preferably the equilibration buffer does not contain calcium, in particular $CaCl_2$).

The washing step is preferably carried out with a washing buffer. The washing buffer preferably is selected from imidazol, histidine, sodium phosphate, sodium citrate, Tris, HEPES, glycine, NaCl and Tween 80. Preferably, the pH of the equilibration buffer is in the range of 6.0 to 7.5, preferably in the range from 6.3 to 6.7. According to one embodiment the concentration of imidazol is about 10-20 mM, the concentration of glycine is about 0.5 to 1%, the concentration of NaCl is about 0.4-1.0 M and the concentration of Tween is about 0.02%. Preferably the pH is about 6.5. Preferably, concentration of $CaCl_2$) in the washing buffer is at most 50 mM. More preferably the washing buffer does not contain calcium, in particular $CaCl_2$).

For eluting the vWF protein from the affinity resin bound complex the binding of the FVIII protein and the vWF protein has to be interrupted. This separation is preferably achieved by contacting the affinity resin bound complex with a solution including calcium ions, for example a gradient of 0 to 0.5 M $CaCl_2$) over a column packed with the affinity resin bound complex and collecting the vWF protein peak as detected by absorbance at 280 nm at the outlet of the column. Alternatively the elution or the vWF protein from the affinity resin can be carried out by stepwise increasing the $CaCl_2$) concentration, preferably 0.15 M $CaCl_2$), more preferably 0.25 M $CaCl_2$) and up to approximately 0.5 M $CaCl_2$). The pH of the vWF separating process is in the range from 6 to 8, preferably 7.4.

According to one embodiment the vWF is eluted with a vWF elution buffer. The vWF elution buffer is selected from imidazol, histidine, sodium phosphate, sodium citrate, Tris, HEPES, glycine, NaCl and Tween 80. Preferably in the elution buffer the concentration of imidazol is about 10 mM, the concentration of glycine is about 0.5 to 1%, the concentration of NaCl is about 0.4 M, the concentration of $CaCl_2$) is about 0.25 M and the concentration of Tween is about 0.02%. If the fraction not binding to the affinity resin after the first simple application is not intended to be used for FVIII deficient plasma etc., the typically 0.25 M $CaCl_2$) as added in the vWF elution buffer can be added in the starting material and/or the equilibration buffer to disrupt the interaction between FVIII and vWF and thus making only FVIII to bind to the affinity resin.

After removal and elution of the vWF in a second step the FVIII protein can be eluted. According to another embodiment of the sixth aspect, the fifth composition comprising the FVIII is eluted by contacting the affinity resin within a second elution buffer comprising an alcohol, in particular ethylene glycol, preferably at a concentration of 50% and a pH between 6 and 8. Preferably, in this regard the affinity resin is VIIISelect.

In case only the vWF is to be enriched/purified the method is carried out without the last elution of the FVIII. Thus according to one embodiment of the sixth aspect the method is for purifying and/or enriching a vWF protein and comprises the steps:
providing a first composition comprising the FVIII protein, which contains at least the light chain of FVIII, and a vWF protein which comprises at least the FVIII binding domain of vWF, wherein the FVIII protein can form a complex with the vWF protein;
performing the separation method according to the first aspect;
optionally applying at least one washing step to the second composition, wherein the second composition contains the affinity resin and a complex of the FVIII protein and the vWF protein; and
eluting a fourth composition comprising the VWF protein from the affinity resin.

According to using the purification and/or the enrichment technique according to the sixth aspect, the composition is obtained comprising the FVIII protein, the vWF protein or a complex of the FVIII protein and the vWF protein. Thus according to the seventh aspect the invention provides a composition comprising a complex of a FVIII protein and a vWF protein or a purified FVIII protein or a purified vWF protein. Thus according to one embodiment the composition comprises a complex of FVIII and vWF protein. According to another embodiment the composition of the sixth aspect comprises a purified FVIII protein. According to a further embodiment the composition of the sixth aspect comprises a purified vWF protein. The purified vWF can be used for addition to a FVIII deficient plasma, in particular an FVIII deficient plasma obtained by a method according to the invention.

The purified FVIII protein or purified vWF protein or the complex of a FVIII protein and a vWF protein may be used in therapy.

Thus, according to a seventh aspect the invention provides a composition according to the sixth aspect for use in therapy. In particular the composition is provided for use in the treatment of bleeding disorders which require an increased coagulation activity. Examples are of such bleeding disorders are different situation of hemophilia A patients and/or vWF deficient patients.

The treatment of bleeding disorders may in particular contain a subcutaneous or intravenous application of the composition.

The invention is further defined by the following examples.

EXAMPLES

Materials Used in the Examples

TABLE 1

Materials

| Name | REF | LOT | Manufacturer |
|---|---|---|---|
| Coatest SP FVIII | 82 4086 63 | N1137466 | Chromogenix |
| Coatest SP4 FVIII | 82 4094 63 | N0434108 | Chromogenix |
| Q.F.A. Thrombin (Bovine) | 0020301800 | N0634945 | Instrumentation Laboratories |
| Von Willebrand Factor Antigen | 0020002300 | B23232 | Instrumentation Laboratories |
| VIIISelect - Immuno affinity gel | Not provided | 1958-029 | GE LifeScience (Provided by Octapharma) |
| FVIII Deficient Plasma, congenital | 5193N | 21223651 | Helena BioSciences |
| Frozen FVIII Deficient Plasma, VisuDep-F | FRDP080125 | 0005-8FDP | Affinity Biologicals |
| FVIII Deficient Plasma | OTXW17 | 546564A | Siemens Healthcare Diagnostic Products |
| rhFVIII Standard | ST-8: C5 | N/A | Octapharma |
| SSC/ISTH Secondary Coagulation Standard | N/A | SSC#4 | NIBSC |
| rhFVIII | 615-588 OgS-12-0273 | GF-Eluat 20130124, 58892-51 | Octapharma |
| Plasma (frozen) | N/A | C419H010/U | Provided by Octapharma |
| Octaplas™ SD | N/A | C419A9521 | Provided by Octapharma |
| Cryo supernatant | N/A | C419G100/U | Provided by Octapharma |
| Tris 10% BSA | TB035 | TTK | Rossix |
| Nuwiq ®, 250 IU vial | | | Octapharma AB |
| Nuwiq ®, 2000 IU vial | | | Octapharma AB |

Example 1—Batch Separation of FVIII from Different Blood Products with VIIISelect Resin 1.1. General VIIISelect is a commercially available gel with expected binding capacity of at least 25 000 IU FVIII/mL. VIIISelect is an affinity resin designed for the purification of recombinant β-domain deleted factor VIII.

Three different start materials were tested: Plasma, Octaplas™ SD and Cryosupernatant.

Plasma and Cryosupernatant were buffered by addition of 0.25 g HEPES/25 mL plasma resulting in a pH of 6.9-7.5. Hepes was not added to Octaplas™ since it is buffered already during production. It contains 0.39 g sodium dihydrogen phosphate dihydrate/kg plasma which is about 2 to 7.5 mmol/L in final product, and 5 g glycin/kg plasma resulting in a pH of 6.9 to 7.4.

1.2. Batch Adsorption Experiments

The VIIISelect resin was prepared using the buffers below:
1. Regeneration Buffer
   0.1 M HAc
2. Wash Buffer
   0.5 M NaCl
3. Elution Buffer
   20 mM L-Histidine,
   0.5 M NaCl,
   20 mM $CaCl_2$),
   in 50% Ethylene Glycol pH 6.4-6.6
4. Equilibration Buffer
   30 g/kg NaCl,
   6.0 g/kg Na-Citrate
   pH 6.4-6.6
5. Storage Solution
   20% Ethanol Unused gels were treated with Buffer 2 followed by Buffer 4. Used gels were treated with; Elution buffer, Regeneration buffer, Wash buffer and Equilibration buffer (buffer 3, 1, 2 and 4) before use. All gels were stored in 20% Ethanol.

2-20 g of affinity resin was treated 3 times with 50 mL of each buffer. For each treatment the buffer was applied to the resin and incubated with the affinity resin for 1 hour during gently stirring. The affinity resin was separated from the blood product using centrifugation at room temperature. The following combinations were investigated and samples were withdrawn at various time points to follow the FVIII binding.

TABLE 2

Overview of tested samples batch adsorption VIIISelect resin

| Starting material | VIIISelect affinity resin (g/25 mL sample) | Temperature (° C.) | Time (hours) |
|---|---|---|---|
| Plasma | 5 | 20-25 | 0-24 |
| Plasma | 1 | 20-25 | 2 × 3 (new gel after 3 hours) |
| Octaplas ™ | 1 | 2-8 | 0-48 |
| Octaplas ™ | 5 | 20-25 | 0-24 |
| Octaplas ™ | 15 | 20-25 | 0-24 |
| Cryo supernatant | 1 | 2-8 | 24 |
| | 1 | 20-25 | 5 |

All three blood products were separated from the gel at the sampling occasion using centrifugation.

Materials from all samples were visually inspected prior to dispensing and freezing and all appeared optically clear with no tendency to clot formation.

1.3. Measurement of FVIII Concentration

The FVIII activity analyses were performed with the Coatest SP FVIII or Coatest $SP_4$ FVIII kits (Chromogenix) using the manual microplate end point method according to the package inserts, expect that more standard dilutions were included in the lower concentration of the FVIII analysis to better be able to detect low concentrations of FVIII.

1.4. Results of the Sample Analysis

From several different batch adsorption experiments in which the effect of gel concentration, temperature and time was investigated it was found that binding of FVIII was improved when any of these three variables were increased.

Figure 2:
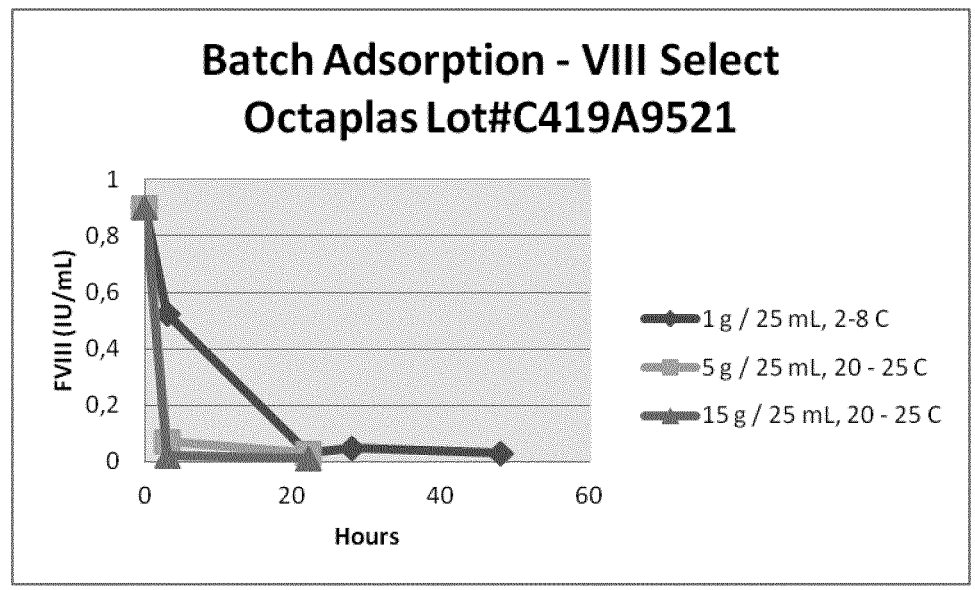
FIG. 2 shows a diagram of a batch adsorption experiment using the VIIISelect and Octaplas™ as starting material. The concentration of FVIII in the blood product is shown on the Y-axis, the time on the X-axis. Different ratios of column material to starting material are indicated.
Figure 3:
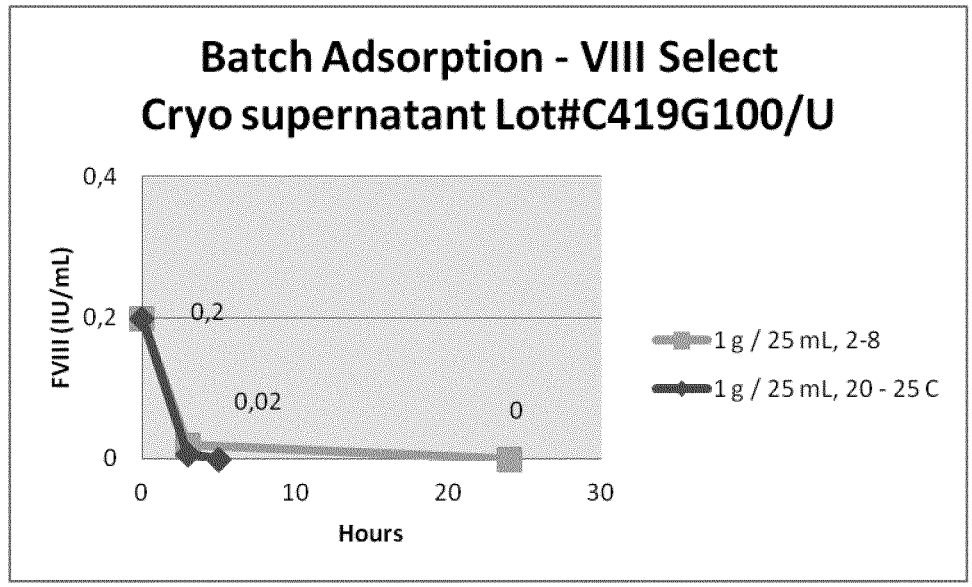
FIG. 3 shows a diagram of a batch adsorption experiment using the VIIISelect and Cryosupernatant as starting material. The concentration of FVIII in the blood product is shown on the Y-axis, the time on the X-axis. Different ratios of column material to starting material are indicated.

The results are shown in FIGS. 1 to 3. Using 5 g VIIISelect/25 mL plasma resulted in a residual FVIII activity of 1.4% for Plasma and 3% for Octaplas™ after 24 hours incubation at 20-25° C. It was not possible to remove all the residual FVIII activity in Octaplas™ even after increasing the gel concentration to 15 g VIIISelect/25 mL Octaplas™. The highest concentration of VIIISelect used for Plasma was 5 g/25 mL.

In contrast, it was possible to bind all FVIII present in the Cryosupernatant using the VIIISelect gel at a concentration of gel of 1 g/25 mL Cryosupernatant. The binding rate increased with an increase in temperature.

Example 2—Column Chromatography FVIII Adsorption Experiments with VIIISelect Resin 2.1. Procedure Like in Example 1 three different blood products were used as starting materials. In each experiment the VIIISelect resin was packed in a XK16 column (GE LifeScience) to a final column volume of 10 mL resin, resulting in a 5 cm bed height. The samples were applied to the columns by two pumps P-50 (0.5 mL/min) and P-1 (0.01-0.05 ml/min) (Pharmacia Biotech). The flow through materials were collected when a stable absorbance at 280 nm had been obtained.

TABLE 3

Setup of VIIISelect column experiments

| Starting material | Flow rate [cm/h] | Flow rate [ml/min] |
|---|---|---|
| Plasma | 15 | 0.5 |
| Octaplas ™ | 15 | 0.5 |
| Octaplas ™ | 15 | 0.5 |
| Octaplas ™ | 0.3-1.5 | 0.01-0.05 |
| Cryosupernatant | 15 | 0.5 |

2.2. Results

Table 4 presents the compiled results. From the data it is clear that the binding of FVIII in Octaplas™ to VIIISelect was strongly dependent on the flow rate used. Thus, the residual FVIII activity dropped from 0.17 to 0.03 IU/mL when decreasing the flow rate from 0.5 mL/min to 0.05 mL/min. It should be noted, though, that a flow rate of 0.05 mL/min (1.5 cm/h) is too low for use in a tentative large scale manufacturing process.

With Plasma as source of FVIII, only a flow rate of 0.5 mL/min was tested and the results were analogous to the batch adsorption experiments, i.e. a somewhat lower residual FVIII activity was obtained as compared to Octaplas™ (0.13 vs 0.17 IU/mL).

In contrast, complete depletion of FVIII activity was obtained from VIIISelect chromatography of Cryosupernatant also when using a flow rate of 0.5 mL/min.

Rechromatography of an Octaplas™ void pool containing 0.17 U/mL FVIII, using a flow rate of 0.5 mL/min. Here, the residual FVIII activity was 0.08 IU/mL, whereas no FVIII activity was detected after chromatography under the same conditions of the Cryosupernatant which had an initial FVIII activity of 0.2 IU/mL.

TABLE 4

Results Column Chromatography experiments

| Startin material | Start (IU/mL) | Void pool (IU/mL) | Flow |
|---|---|---|---|
| Octaplas | 0.9 | 0.17 | 0.5 mL/min (15 cm/h) |
| Rechromatography of void pool 0.17 IU/mL | 0.17 | 0.08 | 0.5 mL/min (15 cm/h) |
| Octaplas | 0.9 | 0.03 | 0.01-0.05 mL/min (0.3-1.5 cm/h) |
| Plasma | 0.7 | 0.13 | 0.5 mL/min (15 cm/h) |
| Cryosupernatant | 0.2 | 0 (Not detectable) | 0.5 mL/min (15 cm/h) |

Example 3—Detailed Analysis of the Blood Products from Examples 1 and 2

Selected preparations from the batch and chromatography experiments were further tested for their suitability as a rhFVIII diluent.

3.1. Determination of FVIII Concentration

A more extensive FVIII analysis were performed on the start materials, reference deficient plasmas and selected final materials. The assay was performed according to the package insert using both the low and the high range. SSC #4 was used as standard and diluted in diluent (high range) and diluent with a constant level (1/81) of congenital deficient plasma (low range). The low range samples were potency assigned vs. the standard diluted in congenital deficient plasma in order to have the same amount of plasma in both the standard and the samples to adhere to the like vs. like principle and to avoid overestimation of the sample FVIII activity. The samples were analyzed as true replicates in two independent assay series.

3.2. Results of FVIII Activity Determination

Three commercially available FVIII deficient plasmas were used as reference (Siemens, Helena Congenital, Affinity). All three reference plasmas had residual FVIII activities that were not detectable or below 0.005 IU/mL (0.5%).

The results are summarized in table 5.

The deficient plasmas prepared from Cryosupernatant by batch adsorption had residual FVIII activities that were not detectable or below 0.005 IU/mL. Plasma incubated with VIIISelect for 24 hours at room temperature (5 g/25 mL plasma) and Octaplas™ incubated with VIIISelect (15 g/25 mL) had residual activities of 0.012-0.014 IU/mL. FVIII depletion from Octaplas™ by chromatography was only possible if very low flow rates were used 0.3-1.5 cm/h (0.01-0.05 mL/min), and even then the residual activity was close to 0.04 when using VIIISelect.

TABLE 5

Results FVIII Analysis with different FVIII deficient plasmas

| | S1 | S2 | S3 | Mean | % of 1 IU/mL |
|---|---|---|---|---|---|
| Start materials | | | | | |
| Octaplas | 0.86 | 1.1 | 0.85 | 0.94 | 94% |
| Plasma | 0.7 | 0.8 | 0.6 | 0.7 | 70% |
| Cryosupernatant | 0.16 | 0.22 | 0.18 | 0.19 | 19% |

TABLE 5-continued

Results FVIII Analysis with different FVIII deficient plasmas

|  | S1 | S2 | S3 | Mean | % of 1 IU/mL |
|---|---|---|---|---|---|
| Reference deficient plasmas |  |  |  |  |  |
| Siemens FVIII DP |  | 0.004 | 0.004 | 0.004 | 0.4% |
| Helena FVIII DP congenital |  | 0 | 0.004 | 0.002 | 0.2% |
| Affinity FVIII DP |  | 0 | 0 | 0 | 0% |
| Sample deficient plasmas |  |  |  |  |  |
| Octaplas, VIIISelect, Batch 15 g/25 mL, 24 h 20-25° C. |  | 0.011 | 0.013 | 0.012 | 1.2% |
| Octaplas, VIIISelect, Chromatography, 0.01-0.05 mL/min, 20-25° C. |  | 0.037 | 0.038 | 0.038 | 3.75% |
| Plasma, VIIISelect, Batch 5 g/25 mL, 24 h, 20-25° C. | 0.0014 |  |  |  |  |
| Cryosupernatant, VIIISelect, Batch 1 g/25 mL, 5 h, 20-25° C. |  | 0.003 | 0.004 | 0.004 | 0.35% |
| Cryosupernatant, VIIISelect, Batch 1 g/25 mL, 24 h, 2-8° C. |  | 0 | 0 | 0 | 0% |

3.3. Determination of vWF Concentration

The vWF concentration was measured in the start materials, reference deficient plasmas and selected materials from the batch and chromatography experiments using the automated latex enhanced immunoassay Von Willebrand Factor Antigen (Instrumentation Laboratories) or a manual version of the same method. The method was adopted to a manual method with kinetic reading and SSC #4 was used as standard. The standard was diluted 1:4 to 1:20 in saline, the samples were diluted 1:8 in saline. Each sample were potency assigned in replicates in two independent assay series.

| Standard/sample | 20 µL |
|---|---|
| Kit buffer | 70 µL |
| Latex reagent | 80 µL |
| Kinetic reading at 405 nm |  |

3.4. Results of the vWF Antigen Determination

Table 6 presents the results of the vWF concentration measurements.

TABLE 6

Results vWF antigen, IU/mL

|  | S1 | S2 | Mean |
|---|---|---|---|
| Control |  |  |  |
| Reference control normal CryoCheck, vWF: Antigen 0.8-1.08 IU/mL | 1.6 | 1.6 | 1.6 |
| Start materials |  |  |  |
| Octaplas | 1.9 | 1.8 | 1.9 |
| Plasma | 1.9 | 2 | 2.0 |
| Cryosupernatant | 0-0.2 | 0-0.2 | 0-0.2 |
| Reference deficient plasmas |  |  |  |
| Siemens FVIII DP | 1.5 | 1.3 | 1.4 |
| Helena FVIII DP congenital | 1.4 | 0.95 | 1.2 |
| Affinity FVIII DP | 0-0.2 | 0-0.2 | 0-0.2 |
| Sample deficient plasmas |  |  |  |
| Octaplas, VIIISelect, Batch 15 g/25 mL, 24 h, 20-25° C. | 1.2 | 1.15 | 1.2 |
| Octaplas, VIIISelect, Chromatography, 0.01-0.05 mL/min, 20-25° C. | 2 | 2.1 | 2.1 |

TABLE 6-continued

Results vWF antigen, IU/mL

|  | S1 | S2 | Mean |
|---|---|---|---|
| Plasma, VIIISelect, Batch 5 g/25 mL, 24 h, 20-25° C. | 1.8 | 1.4 | 1.6 |
| Cryosupernatant, VIIISelect, Batch 1 g/25 mL, 5 h, 20-25° C. | 0-0.2 | 0-0.2 | 0-0.2 |
| Cryosupernatant, VIIISelect, Batch 1 g/25 mL, 24 h, 2-8° C. | 0-0.2 | 0-0.2 | 0-0.2 |

The Cryosupernatant and deficient plasmas derived from Cryosupernatant had a low concentration of vWF antigen. This was also the case for deficient plasma from Affinity Biologicals.

Batch adsorption or column chromatography does not cause any major losses of vWF. Plasma incubated with VIIISelect (5 g/25 mL) had a higher vWF antigen content compared to the reference deficient plasmas (1.6 vs 1.2-1.4 IU/mL).

3.5. Determination of Fibrinogen Concentration

Fibrinogen content was determined using the kit Q.F.A. Thrombin (Instrumentation Laboratories) which is based on the Clauss method. SSC #4 was used as standard. Initial tests showed that the Clauss method could not be used when performing the method manually. The Clauss method is based on the recorded clotting time and the clotting times using the standard Clauss assay was <15 sec resulting in complete clotting prior to start of absorbance measurements.

Clauss Assay

The sample is diluted 1:10 to a volume of 200 µL and incubated at 37° C. for 3-4 min. Then, 100 µL of a thrombin solution (concentration 100 IU/mL) and further incubated at 37° C. The time until clot formation is measured.

Instead of the Clauss assay a modified assay, based on the change in turbidity or light-scattering after complete clotting of the plasma was used:

The sample is diluted 1:10 to a volume of 250 µL. Absorption at at 405 nm is measured. 50 uL of a thrombin solution (concentration 25 IU/mL). Absorption measurement at 405 nm until the absorbance reaches a plateau.

The assay was run at room temperature and each sample were potency assigned in replicates in two independent assay series.

This modified assay, sometimes referred to as the Prothrombin time-derived method has usually a very good correlation to the Clauss method (see ECAT Assay Procedures 2012, Palareti G et al. Clin Chem 1991, Rossi E et al. Thromb Res 1988).

3.6. Results of Fibrinogen Determination

The results for fibrinogen are presented in Table 7.

Batch adsorption using VIIISelect does not seem to cause any losses of Fibrinogen since about the same concentration of Fibrinogen was found before and after batch adsorption. For Octaplas™ incubated with 15 g VIIISelect/25 mL Octaplas™, however, there was a loss of more than 70% (from 2.8 to 0.8 mg/mL). This is most probably explained by the precipitate/clot that was found in the thawed sample.

The obtained control values, 2.5 and 2.7 mg/mL were within the assigned range of 2.33-3.16 mg/mL.

TABLE 7

Results of Fibrinogen determination

|  | S1 | S2 | Mean |
|---|---|---|---|
| Control |  |  |  |
| Reference control normal CryoCheck, Fibrinogen 2.33-3.16 mg/mL | 2.5 | 2.7 | 2.6 |
| Start materials |  |  |  |
| Octaplas | 2.7 | 2.8 | 2.8 |
| Plasma | 3.2 |  | 3.2 |
| Cryosupernatant | 1.6 | 1.7 | 1.7 |
| Reference deficient plasmas |  |  |  |
| Siemens FVIII DP | 2 | 1.9 | 2.0 |
| Helena FVIII DP congenital | 1.6 | 1.6 | 1.6 |
| Affinity FVIII DP | 3 | 2.8 | 2.9 |
| Sample deficient plasmas |  |  |  |
| Octaplas, VIIISelect, Batch 15 g/25 mL, 24 h, 20-25° C. | 0.46 | 1.1 | 0.8* |
| Octaplas, VIIISelect, Chromatography, 0.01-0.05 mL/min, 20-25° C. |  | 1.7 | 1.7 |
| Plasma, VIIISelect, Batch 5 g/25 mL, 24 h, 20-25° C. | 3.3 | 3.2 | 3.3 |
| Cryosupernatant, VIIISelect, Batch 1 g/25 mL, 5 h, 20-25° C. | 2 | 1.9 | 2.0 |
| Cryosupernatant, VIIISelect, Batch 1 g/25 mL, 24 h, 2-8° C. | 2.1 | 2.1 | 2.1 |

3.7. Determination of Factor X Concentration

Factor X activity was determined using an RVV based chromogenic method in which sample FX is activated to FXa by the snake venom RVV. SSC #4 was used as standard. The standard was analysed at dilution 1:20 to 1:200 and the samples were analysed at dilution 1:40. All dilutions were performed in Tris buffer.

The measurement was performed according to the following protocol.

| Standard/sample | 50 µL |
|---|---|
| 3 min, 37° C. |  |
| 0.05 U/mL RVV, 0.05M CaCl₂ | 50 µL |
| 5 min, 37° C. |  |
| FXa Substrate (S-2765) | 50 µL |
| 10 min hydrolysis, 37° C. |  |
| 2% Citric Acid | 50 µL |
| Absorbance reading at 405 nm-490 nm |  |

3.8. Results of Factor X Activity Determination

The results from the Factor X analysis are summarized in table 8.

The table 7 shows that the FVIII depletion process did not have any large effects on the FX activity. All samples including the reference deficient plasmas had FX activities well above 0.5 IU/mL. The FX activity is lower in the Octaplas™ incubated with 15 g VIIISelect/25 mL Octaplas™ and this result is thus in agreement with the results from the vWF and Fibrinogen analyses.

TABLE 8

Results Factor X Activity, IU/mL

|  | Series 1 |
|---|---|
| Start materials |  |
| Octaplas | 1 |
| Plasma | 1.1 |
| Cryosupernatant | 1.1 |

TABLE 8-continued

Results Factor X Activity, IU/mL

|  | Series 1 |
|---|---|
| Reference deficient plasmas |  |
| Siemens FVIII DP | 0.9 |
| Helena FVIII DP congenital | 0.9 |
| Affinity FVIII DP | 0.9 |
| Sample deficient plasmas |  |
| Octaplas, VIIISelect, Batch 15 g/25 mL, 24 h, 20-25° C. | 0.7* |
| Octaplas, VIIISelect, Batch 5 g/25 mL, 24 h, 20-25° C. | 0.9 |
| Plasma, VIIISelect, Batch 5 g/25 mL, 24 h 20-25° C. | 1.1 |
| Cryosupernatant, VIIISelect, Batch 1 g/25 mL, 24 h, 2-8° C. | 1.1 |

Example 4—Determination of the Direct Amidolytic Activity

4.1 Measurement

The presence of any preactivation was checked qualitatively and compared to the SSC #4 by incubating start materials, reference deficient plasmas and selected materials from the batch and chromatograph experiments with two different chromogenic substrates, S-2288 (general serine protease substrate) and S-2366 (thrombin, Factor XIa and APC). All samples were diluted 1:5 and 1:10 in Tris Buffer (TB035 Rossix). The hydrolyisis rate for the samples were compared vs. the hydrolysis rate for the SSC #4 plasma. The following procedure was performed with in some cases minor variations in substrate concentration and incubation temperature to optimize the analytical comparison between the different samples.

| Sample | 50 µL |
|---|---|
| Tris Buffer | 50 µL |
| Substrate 3 mM | 50 µL |
| Kinetic reading at 405 nm |  |

4.2. Results of Direct Amidolytic Activity

Figure 4:
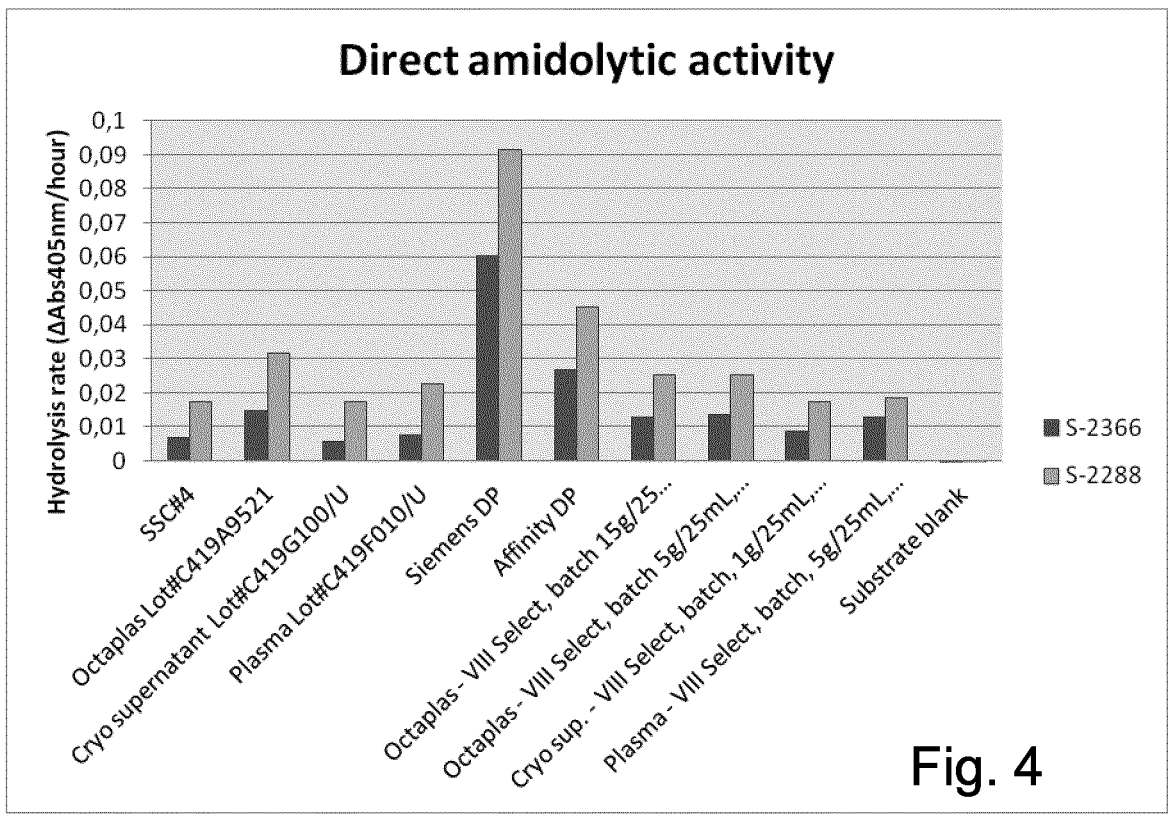
FIG. 4 shows a diagram with the results of the measurement of direct amidolytic activity. On the Y-axis, the hydrolysis rate delta $OD_{405}$ nm/h is shown, on the X-axis, the different tested samples. The left column of each sample represents the hydrolysis rate of S-2366 and the right column the hydrolysis rate of S-2288. The samples are the blood products produced according to examples 1 and 2 and in comparison to commercially available products Siemens DP, Helena and Affinity.

The results are summarized in table 9 and FIG. 4.

The presence of proteases was tested qualitatively by incubation with two chromogenic substrates: S-2288, a general serine protease substrate and S-2366, a sensitive substrate for thrombin, Factor XIa and APC. Overall the results (Table 9) indicate a very limited presence of activated proteases with the exception of Siemens deficient plasma which had clearly higher hydrolysis rates compared to the other samples.

TABLE 9

Results Direct amidolytic activity

|  | S-2366 | | S-2288 | |
|---|---|---|---|---|
| Sample | ΔAbs405 nm/hour | CV % | ΔAbs405 nm/hour | CV % |
| SSC#4 | 0.007 | 0 | 0.017 | 0 |
| Octaplas ™ Lot#C419A9521 | 0.015 | 0.3 | 0.032 | 0 |
| Cryosupernatant Lot#C419G100/U | 0.006 | 2.1 | 0.017 | 23.2 |
| Plasma Lot#C419F010/U | 0.008 | 3.8 | 0.022 | 2.6 |

TABLE 9-continued

Results Direct amidolytic activity

| | S-2366 | | S-2288 | |
|---|---|---|---|---|
| Sample | ΔAbs405 nm/hour | CV % | ΔAbs405 nm/hour | CV % |
| Siemens DP | 0.060 | 1.4 | 0.091 | 0 |
| Helena CongenitalDP | 0.006 | 6.2 | 0.015 | 11.7 |
| Affinity DP | 0.027 | 1.9 | 0.045 | 1.8 |
| Octaplas ™ - VIIISelect, batch 15 g/25 mL, 24 h, RT | 0.013 | 11.5 | 0.025 | 5.3 |
| Octaplas ™ - VIIISelect, batch 5 g/25 mL, 24 h, RT | 0.014 | 2.9 | 0.025 | 2 |
| Cryosup. - VIIISelect, batch, 1 g/25 mL, 24 h, 2-8 | 0.009 | 1.9 | 0.017 | 2.5 |
| Plasma - VIIISelect, batch, 5 g/25 mL, 24 h, RT | 0.013 | 82.1 | 0.019 | 22.6 |
| Substrate blank | −0.001 | 40.4 | −0.001 | 0 |

4.3. Determination of the Stability of rhFVIII

The degree of preactivation was tested implicitly in a reversed stability study by determining the stability of pure rhFVIII spiked into the reference deficient plasmas and the selected materials from the batch and chromatograph experiments according to example 1 and 2. The experimental design was based on the assumption that an increase in preactivation will result in rhFVIII activation and therewith a decrease of the rhFVIII stability. rhFVIII was diluted to a nominal concentration of 1 IU/mL with each FVIII deficient plasma dispensed and frozen at ≤−70° C. A reversed stability study was performed where samples were thawed at 3 h, 5 h and 8 h and compared to samples thawed immediately before start of the assay.

The rhFVIII activity was determined with the Coatest SP FVIII kit using the high range and a manual microplate method. Each sample was analyzed in independently prepared replicates. The standard was diluted to 1 IU/mL in Helena congenital deficient plasma.

4.4. Results of rhFVIII Stability Test Diluted in FVIII Deficient Plasmas

Figure 5:
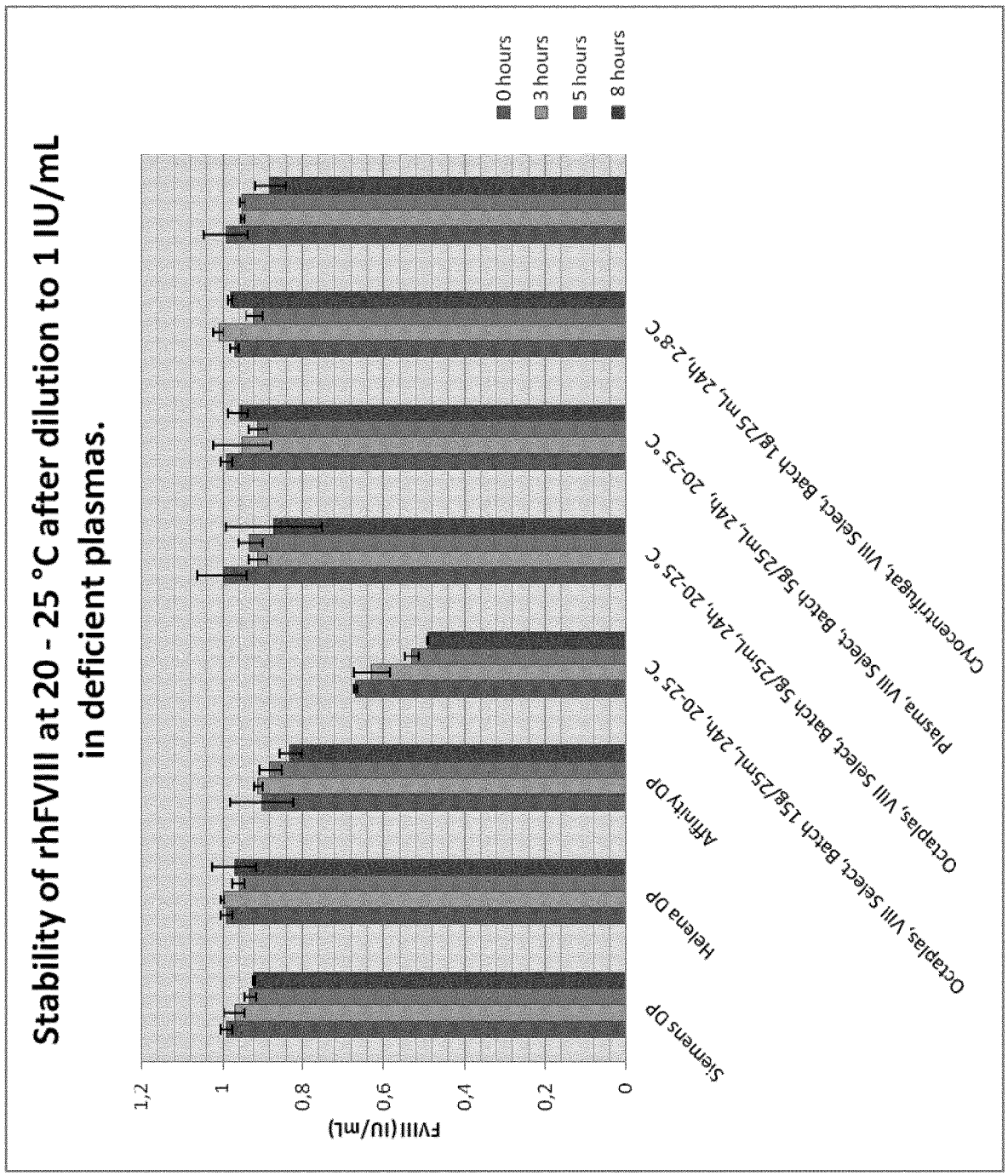
FIG. 5 shows the results of the stability test of rhFVIII in selected blood products obtained according to examples 1 and 2. The column of each sample represents the concentration of FVIII in the sample at different time points, before incubation, after three hours, after five hours and after eight hours.

The results are summarized in Table 10 and FIG. 5.

There were no significant differences of the stability of rhFVIII when diluted to 1 IU/mL in the various deficient plasmas.

The almost identical recovery of rhFVIII at t=0 in the other preparations when potency assigned versus the standard diluted in Helena congenital deficient plasma supports the finding in Example 4.6. that the assay activity is identical for all deficient plasmas.

TABLE 10

Results Stability

| | 0 hours | 3 hours | 5 hours | 8 hours |
|---|---|---|---|---|
| Siemens DP | 0.99 | 0.97 | 0.93 | 0.92 |
| Helena DP | 0.99 | 1 | 0.96 | 0.97 |
| Affinity DP | 0.9 | 0.91 | 0.88 | 0.83 |
| Octaplas ™, VIIISelect, Batch 15 g/25 mL, 24 h, 20-25° C. | 1 | 0.91 | 0.93 | 0.87 |
| Octaplas ™, VIIISelect, Batch 5 g/25 mL, 24 h, 20-25° C. | 0.99 | 0.95 | 0.91 | 0.96 |
| Plasma, VIIISelect, Batch 5 g/25 mL, 24 h, 20-25° C. | 0.97 | 1.01 | 0.92 | 0.98 |
| Cryosupernatant, VIIISelect, Batch 1 g/25 mL, 24 h, 2-8° C. | 0.99 | 0.95 | 0.95 | 0.88 |

4.5. Potency Assignment of rhFVIII Using Different Deficient Plasmas as Dilution Media A concentrated rhFVIII solution was diluted to 1 IU/mL in seven different deficient plasmas and potency assigned versus a standard diluted in the same deficient plasma.

Figure 6:
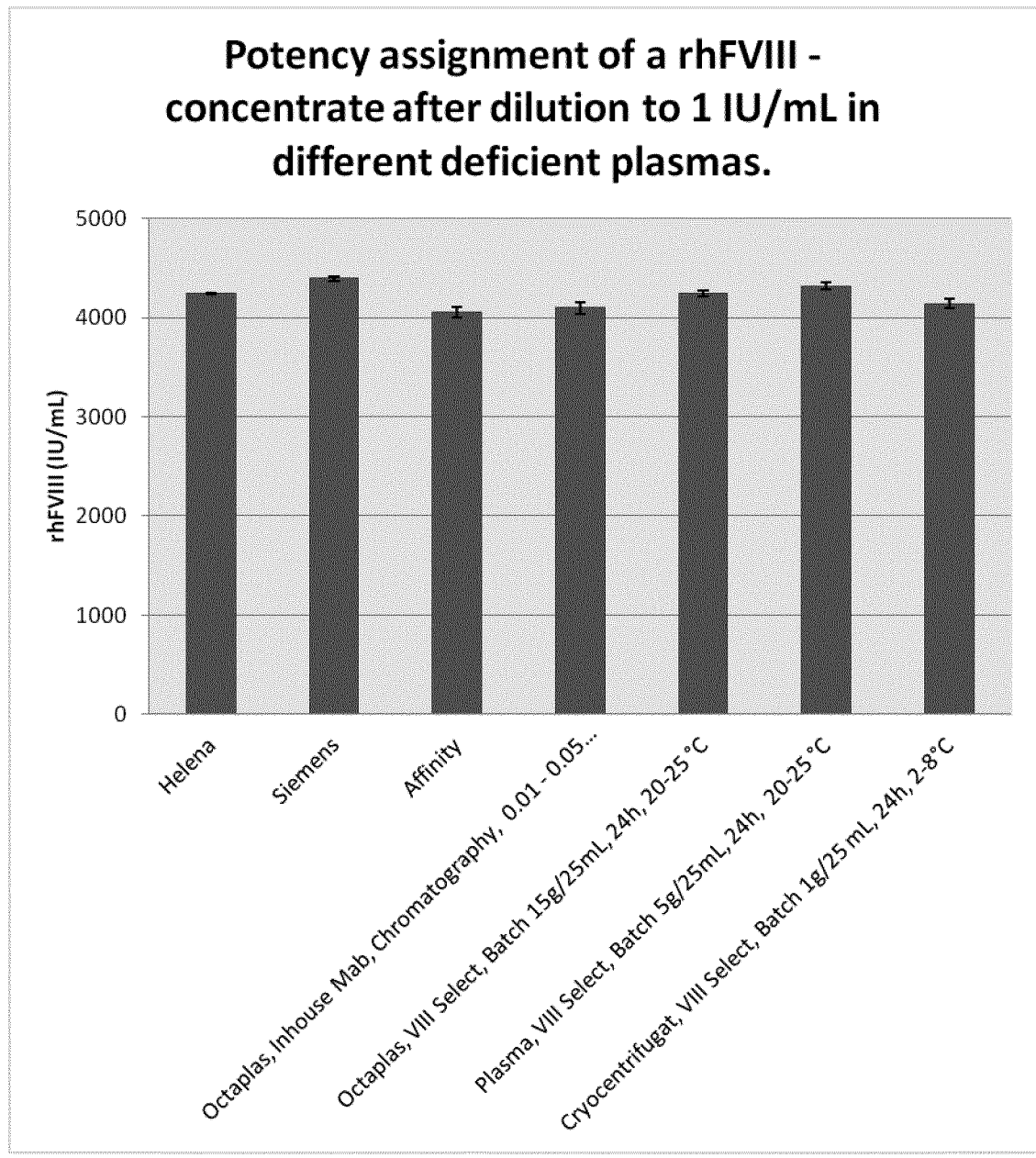
FIG. 6 shows the results of the potency assignment of rhFVIII of three selected blood products obtained in examples 1 and 2 and comparative commercially available FVIII deficient plasmas.

No significant difference in potency assignment could be observed when using the different deficient plasmas as diluents (Table 11, FIG. 6). The mean assigned activity of the rhFVIII preparation was 4213 IU/mL and all mean results for the different deficient plasmas were within +/−4% from the mean, range 4058-4394 IU/mL.

The slope of the standard was not dependent on the deficient plasma. This is due to that the sample and standard was diluted in the same deficient plasma and hence the activity in the assay was lowered for both.

In this experimental set up the potency assignment of rhFVIII was not dependent on the degree of residual FVIII activity in the deficient plasmas since the standard and sample were diluted in the same deficient plasma. Hence the potential contribution from residual FVIII activity is identical for both the sample and the standard. In all cases the contribution from any residual FVIII activity was so low that it did not significantly affect the slopes of the standard curves.

TABLE 11

Results Potency assignment of rhFVIII

| | rhFVIII - IU/mL | | | |
|---|---|---|---|---|
| | Series 1 | Series 2 | Mean | Std dev |
| Helena | 4250 | 4238 | 4244 | 8 |
| Siemens | 4378 | 4410 | 4394 | 23 |
| Affinity | 4096 | 4013 | 4055 | 59 |
| Octaplas ™, VIIISelect, Batch 15 g/25 mL, 24 h, 20-25° C. | 4222 | 4261 | 4242 | 28 |
| Plasma, VIIISelect, Batch 5 g/25 mL, 24 h, 20-25° C. | 4342 | 4296 | 4319 | 33 |
| Cryosupernatant, VIIISelect, Batch 1 g/25 mL, 24 h, 2-8° C. | 4173 | 4105 | 4139 | 48 |

Example 5—Purification of vWF Free of FVIII Activity

The starting material for the purification of vWF was a Wilate a complex of human FVIII and vWF sold by Octapharma under the name Wilate®.

VIIISelect was packed in a XK 16/20 column (GE Healthcare) to a bed height of 4.5 cm equal to a column volume of 9 mL. The flow rate during the experiment was 0.25 mL/min which is equal to 7.5 cm/h. The column was equilibrated with the following equilibration Buffer.

Equilibration Buffer:

| Imidazol | 10 mM |
|---|---|
| Glycin | 0.5-1% |
| NaCl | 0.4M |
| CaCl$_2$ | 0.25M |
| Tween80 | 0.02% |
| pH | 7.4 |

Wilate® was reconstituted in 4 ml 0.25 M CaCl$_2$) for 30 min to disrupt the interaction between FVIII and vWF. Reconstituted Wilate® was applied to the VIIISelect XK 16/20 column with a flow rate of 0.25 ml/min whereby the main part of FVIII bound to the affinity resin and the collected flow trough contained vWF and some other proteins such as fibrinogen etc.

Flow Through Precipitation Buffer

| | |
|---|---|
| Glycine | 2.6M (19.5 g/100 ml) |
| Tris | 20 mM (0.242 g/100 ml) |
| NaCl | 0.3M (1.8 g/100 ml) |

To 1 volume of flowthrough from the VIIISelect column 3.34 volumes of flow through Buffer and 3.13 g NaCl was added to the solution. The high glycin concentration precipitates the vWF molecule. The solution was stirred for 30 min in room temperature and then centrifuged at 600 rpm for 10 min to obtain a vWF containing pellet.

The pellet was reconstituted quickly in the Reconstution Buffer.

Reconstution Buffer

| | |
|---|---|
| Hepes | 40 mM |
| NaCl | 0.15M |
| pH | 7 |
| EDTA | 5 mM |

After reconstitution it was incubated at 28–32° C. for about 10 hours to remove any residual FVIII activity.

Finally, the EDTA was removed using a HiPrep desalting column and an Equilibration buffer with 40 mM Hepes and 0.15 M NaCl pH 7.

The above protocol resulted in a vWF recovery of 20-25% and a residual FVIII activity of less than 0.01 IU FVIII/100 IU vWF Ag.

Example 6—Testing of Different Flow Rates 6.1. Procedure

A limited study was performed to investigate the effect of the flow rate on the residual FVIII activity. Cryosupernatant was applied to an XK16 column packed with VIIISelect, bed height 4 cm, column volume 8 mL. Flow rates from 120-7.5 cm/h were tested (1 mL/min=30 cm/h). Based on the results, a flow rate of 7.5 cm/h (0.25 mL/min) was chosen for the purification of the FVIII deficient plasmas.

6.2. Results

Figure 7:
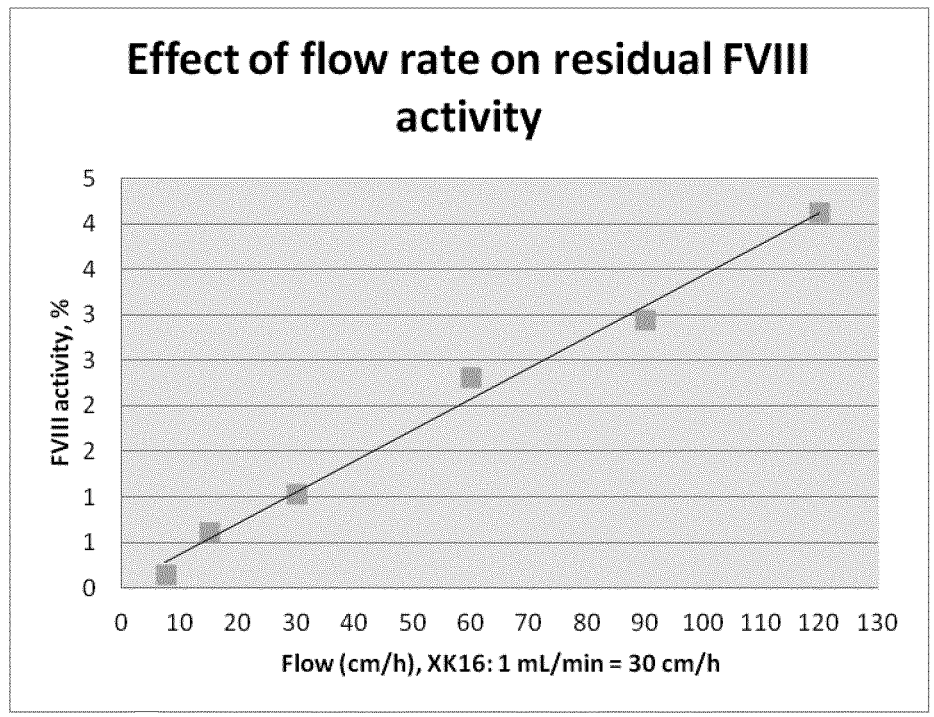
FIG. 7 shows a graph of the results of flow rate tests for continuous column separation of FVIII from Cryosupernatant. In the diagram the Y-axis shows the FVIII activity in percent and the X-axis shows the flow rate in cm/h.

The results are shown in FIG. 7. The residual FVIII activity was linearly related to the flow rate. A flow rate below 10 cm/h provides a reliable production of FVIII deficient plasma with less than 1% FVIII activity.

The used flow rate 7.5 cm/h=0.25 mL/min on a XK16 column with diameter 1.6 cm resulted in a process time of 13 hours when applying 200 mL plasma. 200 mL plasma corresponds to 25 times the column volume and no increased leakage of FVIII was found during the process. The pressure was stable during all column purifications.

Example 7—Production of FVIII Deficient Plasma

Three different batches of FVIII deficient plasma were produced from two different batches of cryosupernatant. The cryosupernatant was thawed in a water bath at room temperature and buffered by addition of 0.25 g Hepes/25 mL plasma resulting in 40 mM Hepes except for one batch which was buffered with 20 mM Hepes (Pre-Pilot 3).

The purification was performed using a XK16 column (GE Lifesciences) packed with VIIISelect, bed height 4 cm, column volume 8 mL and an Äkta Pure 150 chromatography system (GE LifeSciences). 26 g/kg NaCl, 6.0 g/kg Na-Citrate pH 6.4-6.6 was used as equilibration buffer. A flow rate of 7.5 cm/h (0.25 mL/min) was used and 200-250 mL cryosupernatant was applied to each column of each batch resulting in a process time of 13-17 hours.

The FVIII deficient plasma from Pre-Pilot 3 was spiked with vWF, produced according to example 5, to a nominal concentration of 1 IU/ml vWF Ag. The deficient plasmas were dispensed in racks of 96×1 mL and frozen at ≤70° C.

Example 8—Characterization of FVIII Deficient Plasmas 8.1. Determination of the Residual FVIII Activity Residual FVIII activity was measured using the Coatest SP4 FVIII kit (Chromogenix) and the assay was performed according to the Coatest SP4 FVIII package insert using the low range. SSC #4 was used as standard and was diluted in kit buffer. Samples achieved from example 7 were analyzed at dilution 1:81.

8.2. Determination of the vWF Ag Concentration vWF concentration was determined using the von Willebrand Factor Antigen Kit (Instrumentation Laboratories) and the assay was performed using the coagulation instrument ACL TOP 700 with the on board application for the kit. SSC #4 was used as standard.

8.3. Determination of the Fibrinogen Concentration

Fibrinogen content was determined using the kit Q.F.A. Thrombin (Instrumentation Laboratories) and the assay was performed using the coagulation instrument ACL TOP 700 with the on board application for the kit. SSC #4 was used as standard 8.4. Determination of the Factor X Concentration Factor X activity was determined using a RVV based chromogenic method in which sample FX is activated to FXa by the snake venom enzyme RVV-X. SSC #4 was used as standard. The standard was analysed at dilutions 1:20 to 1:200 and the samples were analysed at dilution 1:40. All dilutions were performed in Tris buffer.

Table 12 summarizes the protocol for the determination of the FX concentration.

TABLE 12

| Chromogenic FX method | |
|---|---|
| Standard/sample | 50 µL |
| 3 min, 37° C. | |
| 0.05 U/mL RVV, 0.05M CaCl$_2$ | 50 µL |
| 5 min, 37° C. | |
| FXa Substrate (S-2765) | 50 µL |
| 10 min hydrolysis, 37° C. | |
| 2% Citric Acid | 50 µL |
| Absorbance reading at 405 nm-490 nm | |

8.5. Absorbance Measurements

Absorbance at 280 and 600 nm was measured using an Eppendorf BioPhotometer.

8.6. Results

All samples had a residual FVIII activity of <1%. The Rossix Pre-Pilot 3 was spiked with vWF from about 20-30% to a level of about 100% vWF. This concentration of vWF is comparable to the Siemens deficient plasma tested and around 30% higher compared to the vWF Ag concentration in the congenital FVIII deficient plasma from Helena BioSciences. Pre-Pilot 1 and 2 had a vWF concentration between 20-30%.

The Pre-Pilot plasmas have a slightly (app. 20%) lower fibrinogen concentration compared to the reference plasmas. The reason is most likely that the start material is a Cryo-supernatant plasma, and during the cryoprecipitation step parts of the fibrinogen molecules are co-precipitated. The Factor X activity is normal for all tested deficient plasmas.

As could be noted visually and be expected, the reference plasmas are more turbid, with OD600 1.5-2 fold higher as compared to the Rossix Pre-Pilots. This is related to the fact that the Pre-Pilots originates from a cryoprecipitated plasma and the cryoprecipitate is removed using a centrifugation step which reduces particular matters in the cryosupernatant. Absorbance at 280 nm, which could be used as a measure for protein concentration, is similar or slightly higher in the Rossix Pre-Pilots, probably originating from batch to batch variations between different plasma lots.

TABLE 13

Analytical characterization of deficient plasmas

| | Start material | FVIII activity | vWF Ag (%) | Fibrinogen (g/L) |
|---|---|---|---|---|
| Pre-Pilot 1 | Cryosup. | <1% | 20 | 1.6 |
| Pre-Pilot 2 | Cryosup. | <1% | 33 | 1.6 |
| Pre-Pilot 3 | Cryosup. | <1% | 97 | 1.7 |
| Helena Congenital | | <1% | 65 | 2.1 |
| Siemens | | <1% | 100 | 2.1 |

| | Factor X (%) | OD600 | A280 |
|---|---|---|---|
| Pre-Pilot 1 | 100 | 0.9 | 54 |
| Pre-Pilot 2 | 100 | 0.8 | 50 |
| Rossix Pre-Pilot 3 | 90 | 1.1 | 49 |
| Helena Congenital | 70 | 1.6 | 48 |
| Siemens | Not determined | 1.6 | 45 |

Example 9—Test of Preactivation 9.1. Direct Amidolytic Activity—Experimental Protocol The presence of any preactivation was checked qualitatively by incubating deficient plasmas with two different chromogenic substrates, 4 mM S-2288 (general serine protease substrate) and 2 mM S-2366 (thrombin, Factor XIa and APC). All samples were diluted 1:10 in Tris Buffer (TB035 Rossix).

TABLE 14

Method Direct amidolytic activity

| | |
|---|---|
| Sample diluted 1:10 | 50 µL |
| Tris Buffer | 50 µL |
| Substrate | 50 µL |
| Kinetic reading at 405 nm | |

9.2. Direct Amidolytic Activity—Results

Figure 8:
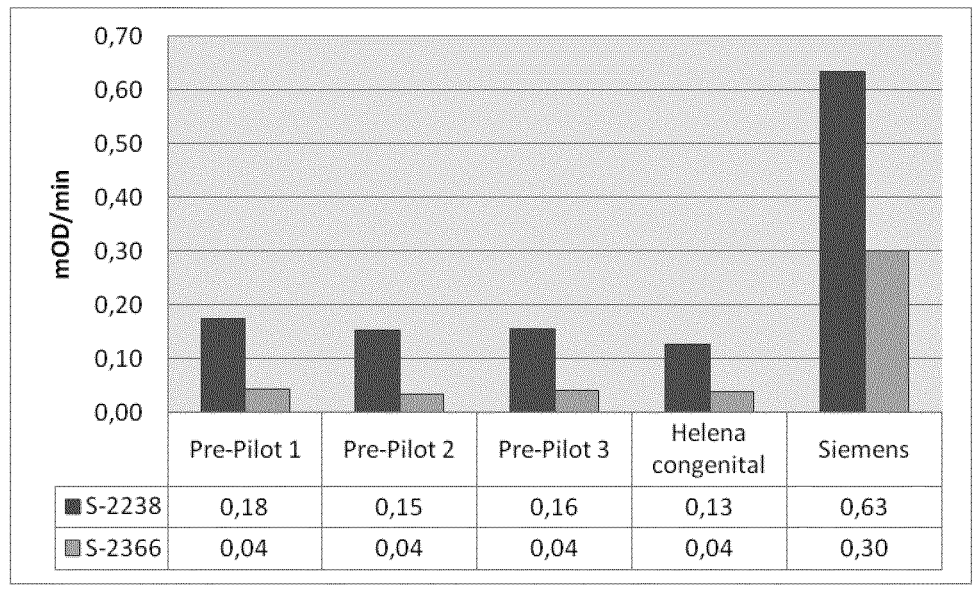
FIG. 8 shows the results of the measurement of the direct amidolytic activity of different plasmas. In the experiment the protease substrates S-2288 and S-2366 were added to different plasmas, namely the modified plasmas (pre-pilot 1, pre-pilot 2 and pre-pilot 3 all purified on VIIISelect chromatography columns) or the reference plasmas, i.e. the commercially available Helena congenital and Siemens were measured. In the column diagram the left column represents the hydrolysis rate of S-2238 and the right column the hydrolysis rate of S-2366.
Figure 9:
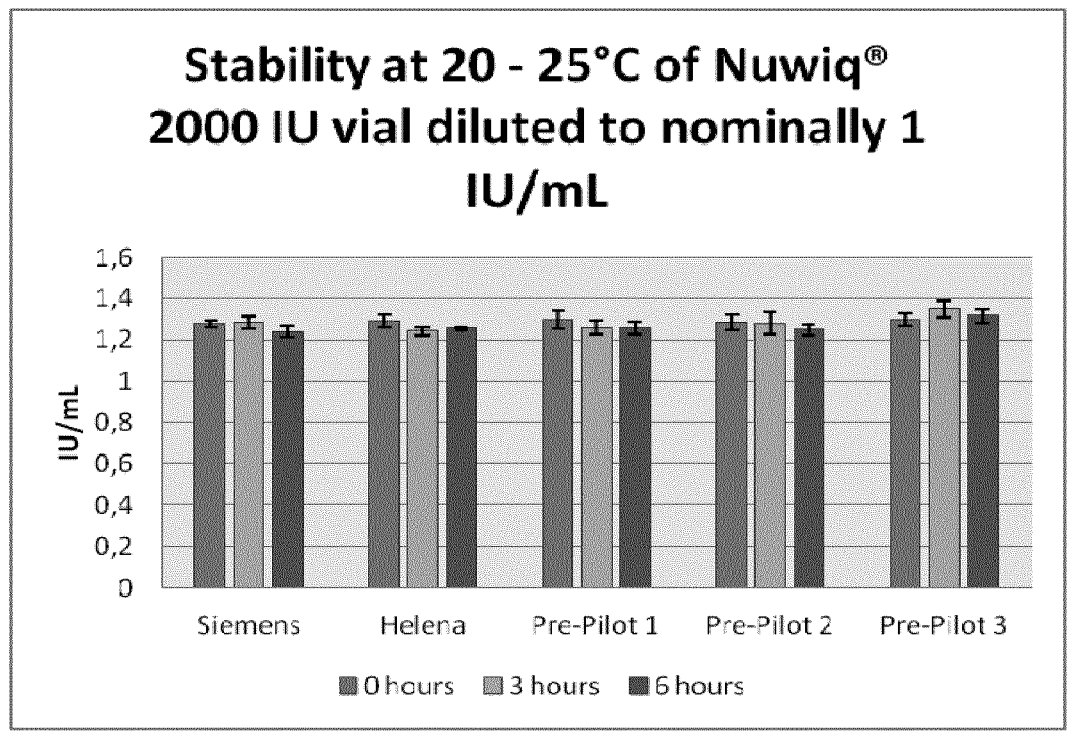
FIG. 9 shows the results of stability measurements of rhFVIII diluted to 1 IU/ml in FVIII deficient plasmas produced according to the invention, i.e. pre-pilot 1, pre-pilot 2 and pre-pilot 3, as well as comparative plasmas (Siemens, Helena).
Figure 10:
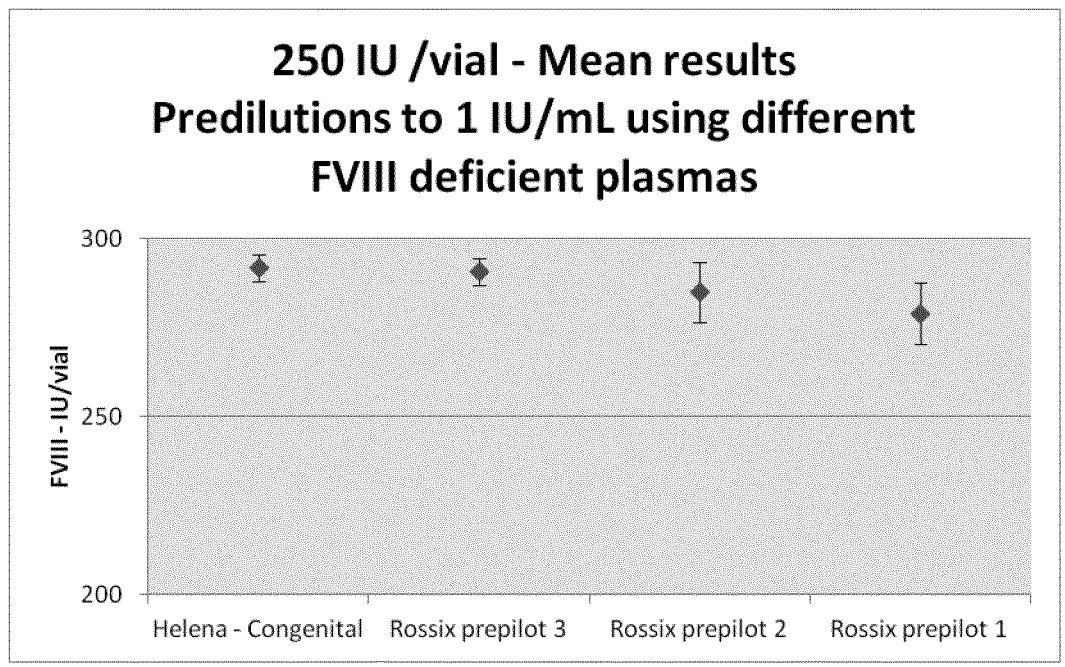
FIG. 10 shows the results of the potency assignment of rhFVIII for the three modified plasmas pre-pilot 3, pre-pilot 2 and pre-pilot 1 and Helena congenital as comparison with rhFVIII in a concentration of 250 IU/ml.
Figure 11:
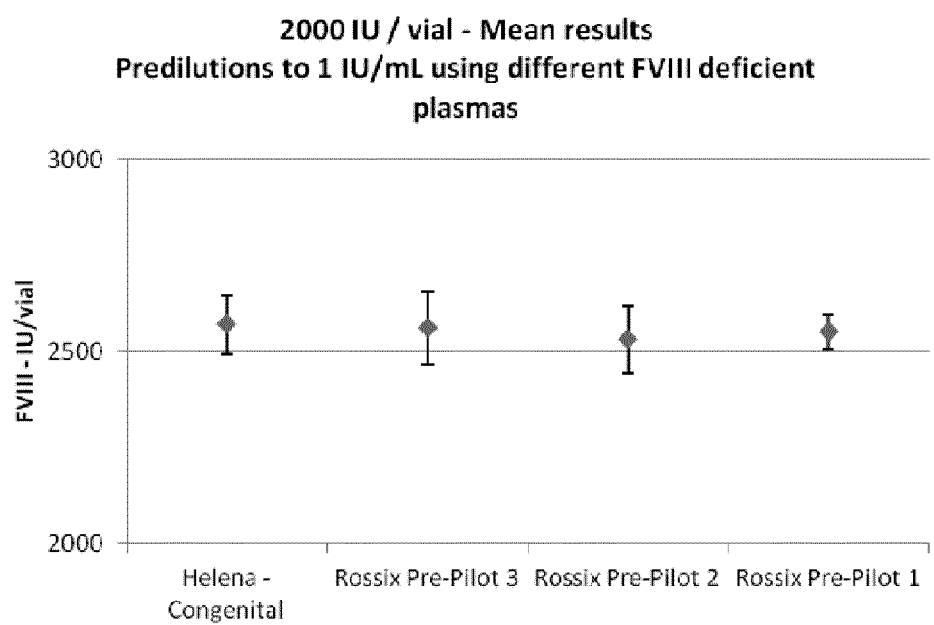
FIG. 11 shows the results of the potency assignment of rhFVIII for the three modified plasmas pre-pilot 3, pre-pilot 2 and pre-pilot 1 and Helena congenital as comparison with rhFVIII in a concentration of 2000 IU/ml.

The results are reported in FIG. 8. The presence of proteases were tested qualitatively by incubation with two chromogenic substrates (S-2288, a general serine protease substrate and S-2366, a sensitive substrate for thrombin, Factor XIa and APC). Overall, the results indicate a very limited presence of activated proteases with the exception of Siemens deficient plasma which had clearly higher hydrolysis rates compared to the other samples.

9.3. Determination of the Stability of rhFVIII

The degree of preactivation was tested implicit in a reversed stability study by determining the stability of pure B-domain deleted rhFVIII spiked into the deficient plasmas.

The experimental design was based on the assumption that an increase in preactivation will result in rhFVIII activation and therewith in a decrease of the rhFVIII stability. Nuwiq® obtained from Octapharma AB, Sweden, 2000 IU/vial was diluted to a nominal concentration of 1 IU/mL with each FVIII deficient plasma, dispensed and frozen at −70° C. A reversed stability study was performed where samples were thawed at 3 h and 6 h and compared to samples thawed immediately before start of the assay.

The rhFVIII activity was determined with the Coatest SP FVIII kit using the high range and a manual microplate method. Each sample was analyzed in true quadruplicates (independently prepared) and potency assigned vs a standard prepared from a pool of the t=0 samples.

9.4. Stability of rhFVIII Diluted in FVIII Deficient Plasmas—Results

There were no significant differences of the stability of Nuwiq® 2000 IU/vial when diluted to nominally 1 IU/mL in the various deficient plasmas. The change in activity after 6 hours storage at 20-25 C was in the range −3 to +2%.

TABLE 15

Stability Nuwiq diluted to 1 IU/mL in deficient plasma

| | FVIII (IU/mL) | | |
|---|---|---|---|
| FVIII deficent plasma | 0 hours | 3 hours | 6 hours |
| Pre-Pilot 1 | 1.30 | 1.26 | 1.26 |
| Pre-Pilot 2 | 1.29 | 1.28 | 1.25 |
| Pre-Pilot 3 | 1.30 | 1.35 | 1.32 |
| Helena | 1.29 | 1.24 | 1.26 |
| Siemens | 1.28 | 1.29 | 1.24 |

9.5. Potency Assignment of rhFVIII (Nuwiq® 250 IU Vial and 2000 IU Vial) after Dilution to 1 IU/mL in the Different Deficient Plasmas.

The results of the potency assignment are shown tables 15 and 16 as well as FIGS. 13 and 14. All assay series were approved for parallelism, regression and linearity. There was no significant difference in variation or potency assignment of the 2000 IU/vial between the different deficient plasmas. The 250 IU/vial showed a larger variation and a 2-5% lower assigned potency when prediluted in Pre-Pilot 1 and 2. These are the two Pre-Pilots with low vWF Ag concentration and an explanation to the slightly lower results might be that a lower presence of vWF Ag results in less stable rhFVIII dilutions.

The obtained potencies of about 290 IU/vial and 2550 IU/vial differs from the nominal activity of 250 IU/vial and 2000 IU/vial and corresponds to +16% and +28% respectively.

The dose-response of the standard and samples were similar for all deficient plasmas used.

TABLE 15

Potency assignment - 250 IU vial

| | Helena Deficient plasma | | | Rossix Pre-Pilot 3 | | | Rossix Pre-Pilot 2 | | | Rossix Pre-Pilot 1 | | |
|---|---|---|---|---|---|---|---|---|---|---|---|---|
| | Lower Limit | Esti-mate | Upper Limit | Lower Limit | Esti-mate | Upper Limit | Lower Limit | Esti-mate | Upper Limit | Lower Limit | Esti-mate | Upper Limit |
| Series 1 | | | | | | | | | | | | |
| Series 2 | 280 | 290 | 300 | 283 | 288 | 292 | 271 | 276 | 281 | 266 | 271 | 277 |
| Series 3 | 280 | 289 | 298 | 280 | 289 | 296 | 282 | 286 | 290 | 271 | 278 | 286 |
| Series 4 | 288 | 296 | 304 | 288 | 295 | 302 | 285 | 293 | 301 | 282 | 288 | 294 |
| Mean Result | | 292 | | | 291 | | | 285 | | | 279 | |
| Standard Deviation | | 4 | | | 4 | | | 9 | | | 9 | |

15

TABLE 16

Potency assignment - 2000 IU vial

| | Helena Deficient plasma | | | Rossix Pre-Pilot 3 | | | Rossix Pre-Pilot 2 | | | Rossix Pre-Pilot 1 | | |
|---|---|---|---|---|---|---|---|---|---|---|---|---|
| | Lower Limit | Esti-mate | Upper Limit | Lower Limit | Esti-mate | Upper Limit | Lower Limit | Esti-mate | Upper Limit | Lower Limit | Esti-mate | Upper Limit |
| Series 1 | 2550 | 2640 | 2740 | 2400 | 2480 | 2570 | 2480 | 2560 | 2640 | 2470 | 2550 | 2630 |
| Series 2 | 2450 | 2520 | 2600 | 2560 | 2630 | 2710 | 2380 | 2540 | 2720 | 2430 | 2490 | 2550 |
| Series 3 | 2580 | 2630 | 2700 | 2550 | 2650 | 2750 | 2490 | 2620 | 2760 | 2530 | 2600 | 2670 |
| Series 4 | 2410 | 2490 | 2580 | 2370 | 2470 | 2570 | 2320 | 2410 | 2510 | 2470 | 2560 | 2650 |
| Mean Result | | 2570 | | | 2560 | | | 2530 | | | 2550 | |
| Standard Deviation | | 76 | | | 96 | | | 88 | | | 45 | |

REFERENCES

1. Farrugia et al., Biotechnology and plasma fractionation industry. The impact of advances in the production of coagulation FVIII. Biotechnology, 1993, vol. 3, No. 1
2. Fay, Factor VIII: Function and structure, International Journal of Hematology vol. 83 2006, pp. 103-108
3. Metal ion-independent association of Factor VIII subunits and the roles of calcium and copper ions for cofactor activity and inter-sub-unit affinity, Biochemistry 2001, vol. 40, 10293-10300
4. Wang et al., Coagulation Factor VIII; structure and stability, International Journal of pharmaceutics 2003, Vol. 259, pp. 1-15.
5. Furlan, Von Willebrand factor: molecular size and functional activity, Ann Hematol. 1996 vol 72(6), pp 341-348
6. Svensson et al., Evaluation of the metal binding site in a recombinant coagulation factor VIII identifies two sites with unique metal binding sites, Biological Chemistry 2013; vol. 394(6), pp. 761-765
7. Eriksson et al., The manufacturing process for B-domain deleted recombinant FVIII, Seminars in Hematology, 2001, Vol 38, No 2, Suppl. 4 pp. 24-31
8. Girma et al., Assay of Factor VIII antigen (FVIII:CAg) in 294 Haemophilia A patients by a new commercial ELISA using monoclonal antibodies, Haemophilia, 1998, vol. 4, pp. 98-103
9. Fischer et al., Structural analysis of recombinant von Willebrand factor: identification of hetero- and homo-dimers, FEBS Letters 1994, vol. 351, pp 345-348
10. ECAT Assay Procedures a Manual of Laboratory Techniques, Springer October 2012
11. Palareti et al., Fibrinogen assays: a collaborative study of six different methods, Clinical Chemistry, 1991; vol 37 pp 714-19
12. Rossi et al. Method for the determination of functional (clottable) fibrinogen by the new family of ACL coagulometers. Thromb Res 1988, vol. 52, pp 453-468

The invention claimed is:

1. A method for separating a Factor VIII (FVIII) protein from a first composition comprising the FVIII protein, which contains at least the light chain of FVIII, and a von-Willebrand-Factor (vWF) protein which comprises at least the FVIII binding domain of vWF, wherein the FVIII protein can form a complex with the vWF protein, the method comprising the steps:

contacting the first composition with an affinity resin comprising a ligand and a matrix, wherein the ligand has an affinity to the light chain of FVIII, and separating the affinity resin from the mixture to obtain a modified first composition and a second composition, wherein the second composition contains the affinity resin and a complex of the FVIII protein and the vWF protein.

2. The method according to claim 1, wherein the FVIII protein is selected from the group consisting of human plasma derived FVIII, an FVIII derivative naturally occurring in human blood, recombinant human full length FVIII and recombinant human B-domain depleted FVIII.

3. The method according to claim 1, wherein the vWF protein is selected from the group consisting of a human plasma derived vWF multimer, a human plasma derived vWF monomer and a recombinant human full length vWF.

4. The method according to claim 1, wherein the ligand is a polypeptide.

5. The method according to claim 4, wherein the ligand is an antibody Fab fragment.

6. The method according to claim 5, wherein the matrix is composed of highly cross-linked agarose.

7. The method according to claim 1, wherein separating is performed continuously over a packed column and the flow rate of the first and/or modified first composition is equal to or below 30 cm/h, equal to or below 15 cm/h, equal to or below 10 cm/h, or equal to or below 7.5 cm/h.

8. The method according to claim 7, wherein the concentration of the FVIII protein in the first composition based on the total volume of the first composition is equal to or below 1 IU/mL, equal to or below 0.7 IU/mL, equal to or below 0.4 IU/mL or equal to or below 0.2 IU/mL.

9. The method according to claim 7, wherein the ratio of the volume of the first composition to the volume of the resin is in the range from 5:1 to 100:1, in the range from 10:1 to 70:1, in the range from 10:1 to 50:1, or in the range from 20:1 to 40:1.

10. The method according to claim 1, wherein the first composition comprises a blood product, or a human blood product and the blood product is selected from whole blood, plasma and serum.

11. The method according to claim 10, wherein the blood product is a plasma.

12. The method according to claim 1, wherein the FVIII protein and/or the vWF protein are recombinantly expressed proteins.

13. A method for producing a modified blood product, comprising the steps:
   providing a first composition comprising a blood product, wherein the blood product is plasma;
   performing the separation of FVIII according to claim 1; and
   collecting the modified first composition comprising the modified blood product.

14. The method according to claim 13, further comprising adding an exogenous vWF protein essentially free of FVIII to the plasma.

15. The method according to claim 5, wherein the ligand is a 13 kD Fab fragment.

16. The method according to claim 6, wherein the affinity resin is VIIISelect.

17. The method according to claim 11, wherein the blood product is a pretreated plasma or a chemically virus inactivated plasma.

* * * * *